(12) United States Patent
Lee et al.

(10) Patent No.: US 6,929,730 B2
(45) Date of Patent: Aug. 16, 2005

(54) TWO DIMENSIONAL MICROFLUIDIC GENE SCANNER

(76) Inventors: Cheng Sheng Lee, 3823 Grosvenor Dr., Ellicott City, MD (US) 21042; Donald Lad DeVoe, 5619 Sonoma Rd., Bethesday, MD (US) 20817

( * ) Notice: Subject to any disclaimer, the term of this patent is extended or adjusted under 35 U.S.C. 154(b) by 0 days.

(21) Appl. No.: 10/135,385

(22) Filed: May 1, 2002

(65) Prior Publication Data

US 2002/0195342 A1 Dec. 26, 2002

Related U.S. Application Data

(60) Provisional application No. 60/287,801, filed on May 1, 2001.

(51) Int. Cl.⁷ .................... G01N 27/447; G01N 27/453
(52) U.S. Cl. ......................................... 204/451; 204/601
(58) Field of Search ................................. 204/451, 453, 204/456, 601, 604, 605

(56) References Cited

U.S. PATENT DOCUMENTS

| | | | |
|---|---|---|---|
| 4,576,702 A | | 3/1986 | Peck et al. ................ 204/299 |
| 5,066,377 A | * | 11/1991 | Rosenbaum et al. ........ 204/466 |
| 5,102,518 A | | 4/1992 | Doering et al. .......... 204/180.1 |
| 5,217,591 A | | 6/1993 | Gombocz et al. ........... 204/299 |
| 5,245,185 A | | 9/1993 | Busch et al. ............... 250/288 |
| 5,275,710 A | | 1/1994 | Gombocz et al. ........... 204/299 |
| 5,505,831 A | | 4/1996 | Liao et al. .................. 204/451 |
| 5,541,420 A | | 7/1996 | Kambara .................... 204/602 |
| 5,587,062 A | | 12/1996 | Togawa et al. ............. 204/613 |
| 5,599,432 A | | 2/1997 | Manz et al. ................ 204/451 |
| 5,635,045 A | | 6/1997 | Alam ......................... 204/462 |
| 5,795,720 A | * | 8/1998 | Henco et al. .................. 435/6 |
| 5,916,428 A | | 6/1999 | Kane et al. ................. 204/601 |
| 5,957,579 A | | 9/1999 | Kopf-Sill et al. ........... 366/340 |
| 6,013,165 A | * | 1/2000 | Wiktorowicz et al. ...... 204/456 |
| 6,068,752 A | | 5/2000 | Dubrow et al. ............. 204/604 |
| 6,274,089 B1 | | 8/2001 | Chow et al. ................ 422/101 |
| 6,406,604 B1 | * | 6/2002 | Guzman ..................... 204/601 |
| 6,540,896 B1 | * | 4/2003 | Manz et al. ................ 204/451 |
| 6,592,735 B1 | * | 7/2003 | Meier et al. ................ 204/621 |

FOREIGN PATENT DOCUMENTS

| | | | |
|---|---|---|---|
| WO | WO 94 28406 | 12/1994 | ......... G01N/27/447 |
| WO | 98/00231 A1 * | 1/1998 | ............ B01J/19/00 |
| WO | WO 00/57170 | 9/2000 | ......... G01N/27/447 |

OTHER PUBLICATIONS

CAPLUS abstract for Domingo (ES 2078878 A1).

CAPLUS abstract for Grushka et al. ("Effect of Temperature Gradients on the Efficiency of Capillary Zone Electrophoresis Separations", *Analytical Chemistry*, (1989), 61(3); 241–6).

(Continued)

*Primary Examiner*—Alex Noguerola
(74) *Attorney, Agent, or Firm*—Pillsbury Winthrop LLP

(57) ABSTRACT

One embodiment of the invention relates to a microfluidic apparatus for performing two dimensional biomolecular separations. According to one aspect of the invention, after a first dimension separation in a first microchannel, the sample material is electrokinetically and simultaneously transferred to an array of microchannels in the second dimension (e.g., by changing the electric potentials at the reservoirs connected to the microchannels). Preferably any separation accomplished in the first dimension is completely retained upon transfer to the second dimension. According to another aspect of the invention, the separation in the second dimension is performed using a temperature gradient (e.g., a spatial or temporal temperature gradient). According to one embodiment of the invention, the biomolecular material comprises DNA and the first dimension separation is a sized-based separation and the second dimension separation is a sequence-based separation.

73 Claims, 11 Drawing Sheets

OTHER PUBLICATIONS

CAPLUS abstract for Guttman et al. ("Effect of Temperature on the Separation of DNA Restriction Fragments in Capillary Gel Electrophoresis", *Journal of Chromatography*, (1991), 559(1–2); 285–94).

CAPLUS abstract for Zhang et al. ("The Effect of Column Temperature on the Migration Teimes of Peptides in Free-Solution Capillary Electrophoresis", *Journal of Liquid Chromatography*, (1993), 16(17); 3689–97).

Gao et al., "High–Throughput Detection of Unknown Mutations by Using Multiplexed Capillary Electrophoresis with Poly(vinylpyrrolidone) Solutions", *Analytical Chemistry*, vol. 72, No. 11, Jun. 1, 2000, pp. 2499–2506.

Gottschlich et al., "Two–Dimensional Electrochromatography/Capillary Electrophoresis on a Microchip", *Analytical Chemistry*, vol. 73, No. 11, Jun. 1, 2001, pp. 2669–2674.

Rocklin et al., "A Microfabricated Fluidic Device for Performing Two–Dimensional Liquid–Phase Separations", *Analytical Chemistry*, vol. 72, No. 21, Nov. 1, 2000, pp. 5244–5249.

Becker et al., "Planar Quartz Chips with Submicron Channels for Two–Dimensional Capillary Electrophoresis Applications", *J. Micromech. Microeng.*, vol. 8, 1998, pp. 24–28.

Liu et al., "Two–Dimensional Separations: Capillary Electrophoresis Coupled to Channel Gel Electrophoresis", *Analytical Chemistry*, vol. 68, No. 22, Nov. 15, 1996, pp. 3928–3933.

Hillenkamp et al., "Matrix–Assisted Laser Desorption/Ionization Mass Spectrometry of Biopolymers", *Analytical Chemistry*, vol. 63, No. 24, Dec. 15, 1991, pp. 1193A–1202A.

Fenselau, "Maldi–MS and Strategies for Protein Analysis", *Analytical Chemistry News & Features*, vol. 69, Nov. 1, 1997, pp. 661A–665A.

Kebarle et al., "From Ions in Solution to Ions in the Gas Phase—The Mechanism of Electrospray Mass Spectrometry", *Analytical Chemistry*, vol. 65, No. 22, Nov. 15, 1993, pp. 972A–986A.

Yates, III, "Special Feature: Tutorial: Mass Spectrometry and the Age of the Proteome", *Journal of Mass Spectrometry*, vol. 33, 1998, pp. 1–19.

Klose et al., "Two–Dimensional Electrophoresis of Proteins: An Updated Protocol and Implications for a Functional Analysis of the Genome", *Electrophoresis*, vol. 16, 1995, pp. 1034–1059.

Jungblut et al., "Resolution Power of Two–Demensional Electrophoresis and Identification of Proteins from Gels", *Electrophoresis*, vol. 17, 1996, pp. 839–847.

Rabilloud, "Detecting Proteins Separated by 2–D Gel Electrophoresis", *Analytical Chemistry*, vol. 72, Jan. 1, 2000, pp. 48A–55A.

Shevchenko et al., "Mass Spectrometric Sequencing of Proteins from Silver–Stained Polyacrylamide Gels", *Analytical Chemistry*, vol. 68, No. 5, Mar. 1, 1996, pp. 850–858.

Shevchenko et al., "Linking Genome and Proteome by Mass Spectrometry: Large–Scale Identification of Yeast Proteins from Two Dimensional Gels", *Proc. Natl. Acad. Sci. USA*, vol. 93, Dec. 1996, pp. 14440–14445.

Gygi et al., "Evaluation of Two–Dimensional Gel Electrophoresis–Based Proteome Analysis Technology", *Proc. Natl. Acad. Sci. USA*, vol. 97, No. 17, Aug. 15, 2000, pp. 9390–9395.

Smith, "Probing Proteomes—Seeing the Whole Picture?", *Nature Biotechnology*, vol. 18, Oct. 2000, pp. 1041–1042.

Burgi et al., "Optimization in Sample Stacking for High-Performance Capillary Electrophoresis", *Analytical Chemistry*, vol. 63, No. 18, Sep. 15, 1991, pp. 2042–2047.

Chien et al., "On–Column Sample Concentration Using Field Amplification in CZE", *Analytical Chemistry*, vol. 64, No. 8, Apr. 15, 1992, pp. 489A–496A.

Chien et al., "Sample Stacking of an Extremely Large Injection Volume in High–Performance Capillary Electrophoresis", *Analytical Chemistry*, vol. 64, No. 9, May 1, 1992, pp. 1046–1050.

Burgi et al., "On–Line Sample Preconcentration for Capillary Electrophoresis", in *Handbook of Capillary Electrophoresis*, Edited by James P. Landers, CRC Press, 1997, pp. 479–493.

Ramsey et al., "Generating Electrospray from Microchip Devices Using Elctroosmotic Pumping", *Analytical Chemistry*, vol. 69, No. 6, Mar. 15, 1997, pp. 1174–1178.

Oleschuk et al., "Analytical Microdevices for Mass Spectrometry", *Trends in Analytical Chemistry*, vol. 19, No. 6, 2000, pp. 379–388.

Gatlin et al., "Protein Identification at the Low Femtomole Level from Silver–Stained Gels Using a New Fritless Electrospray Interface for Liquid Chromatography—Microspray and Nanospray Mass Spectrometry", *Analytical Biochemistry*, vol 263, 1998, Article No. AB982809, pp. 93–101.

Scheler et al., "Peptide Mass Fingerprint Sequence Coverage from Differently Stained Proteins on Two–Dimensional Electrophoresis Patterns by Matrix Assisted Laser Desorption/Ionization–Mass Spectrometry (MALDI–MS)", *Electrophoresis*, vol. 19, 1998, pp. 918–927.

Ramsamooj et al., "Differential Expression of Proteins in Radioresistant and Radiosensitive Human Squamous Carcinoma Cells", *Journal of the National Cancer Institute*, vol. 84, No. 8, Apr. 15, 1992, pp. 622–628.

Wilkins et al., "Proteome Research: New Frontiers in Functional Genomics", Published by Springer, Berlin, 1997, pp. 187–219.

Ostergaard et al., "Psoriasin (S100A7): A Putative Urinary Marker for the Follow–Up of Patients with Bladder Squamous Cell Carcinomas", *Electrophoresis*, vol. 20, 1999, 349–354.

Page et al., "Proteomic Definition of Normal Human Luminal and Myoepithelial Breast Cells Purified from Reduction Mammoplasties", *Proc. Natl. Acad. Sci. USA*, vol .96, No. 22, Oct. 26, 1999, pp. 12589–12594.

Wilm et al., "Femtomole Sequencing of Proteins from Polyacrylamide Gels by Nano–Electrospray Mass Spectrometry", *Nature*, vol. 379, Feb. 1, 1996, pp. 466–469.

Lottspeich, "Proteome Analysis: A Pathway to the Functional Analysis of Proteins", *Angew. Chem. Int. Ed.*, vol. 38, 1999, pp. 2476–2492.

Pandey et al., "Proteomics to Study Genes and Genomes", *Nature*, vol. 405, Jun. 15, 2000, pp. 837–846.

Binz et al., "A Molecular Scanner to Automate Proteomic Research and to Display Proteome Images", *Analytical Chemistry*, vol. 71, No. 21, Nov. 1, 1999, pp. 4981–4988.

Bienvenut et al., "Toward a Clinical Molecular Scanner for Proteome Research: Parallel Protein Chemical Processing Before and During Western Blot", *Analytical Chemistry*, vol. 71, No. 21, Nov. 1, 1999, pp. 4800–4807.

Hjerten et al., "Adaptation of the Equipment for High–Performance Electrophoresis to Isoelectric Focusing", *Journal of Chromatography*, vol. 346, 1985, pp. 265–270.

Hjerten et al., "Carrier–Free Zone Electrophoresis, Displacement Electrophoresis, and Isoelectric Focusing in a High–Performance Electrophoresis Apparatus", *Journal of Chromatography*, vol. 403, 1987, pp. 47–61.

Kilar et al., "Fast and High Resolution Analysis of Human Serum Transferrin by High Performance Isoelectric Focusing in Capillaries", *Electrophoresis*, vol. 10, 1989, pp. 23–29.

Yefimov et al., "Transfer of SDS–Proteins from Gel Electrophoretic Zones into Mass Spectrometry, Using Electrolution of the Band into Buffer Without Sectioning of the Gel", *Journal of Biochemical and Biophysical Methods*, vol. 42, 2000, pp. 65–78.

Yefimov et al., "Recovery of Sodium Dodecyl Sulfate–Proteins from Gel Electrophoretic Bands in a Single Electroelution Step for Mass Spectrometry Analysis", *Analytical Biochemistry*, vol. 284, 2000, pp. 288–295.

Galvani et al., "Letter to the Editor", *Rapid Communications in Mass Spectrometry*, vol. 14, 2000, pp. 721–723.

Clarke et al., "One Step Microelectroelution Concentration Method for Efficient Coupling of Sodium Dodecylsulfate Gel Electrophoresis and Matrix–Assisted Laser Desorption Time–of–Flight Mass Spectrometry for Protein Analysis", *Journal of the American Society of Mass Spectrometry*, vol. 9, 1998, pp. 88–91.

Tomlinson et al., Improved On–Line Membrane Preconcentration—Capillary Electrophoresis (mPC–CE), *Journal of High Resolution Chromatography*, vol. 18, Jun. 1995, pp. 381–383.

Timperman et al., "Peptide Electroextraction for Direct Coupling of In–Gel Digests with Capillary LC–MS/MS for Protein Identificaiton and Sequencing", *Analytical Chemistry*, vol. 72, No. 17, Sep. 1, 2000, pp. 4115–4121.

Guttman et al., "Rapid Analysis of Covalently and Non–Covalently Fluorophore–Labeled Proteins Using Ultra–Thin–Layer Sodium Dodecylsulfate Gel Electrophoresis", *Journal of Chromatography A*, vol. 894, 2000, pp. 329–335.

Csapo et al., "Automated Ultra–Thin–Layer SDS Gel Electrophoresis of Proteins Using Noncovalent Fluorescent Labeling", *Analytical Chemistry*, vol. 72, No. 11, Jun. 1, 2000, pp. 2519–2525.

Shoji et al., "Electrophoretic Recovery of Proteins from Polyacrylamide Gel", *Journal of Chromatography A*, vol. 698, 1995, pp. 145–162.

* cited by examiner

TWO DIMENSIONAL MICROFLUIDIC GENE SCANNER

CROSS-REFERENCE TO RELATED APPLICATIONS

This application claims priority from U.S. Provisional Patent Application Ser. No. 60/287,801, filed May 1, 2001, which is incorporated herein by reference in its entirety.

The U.S. Government has a paid-up license in this invention and the right in limited circumstances to require the patent owner to license others on reasonable terms as provided for by the terms of Grant Numbers: R43CA092819, and R43GM062738, awarded by the National Institutes of Health, and Grant Number DAAH01-02-C-R136, awarded by the Defense Advanced Research Projects Agency.

FIELD OF THE INVENTION

The invention relates to a system and method for using a microfluidic apparatus for performing two dimensional separations of biomolecular materials.

BACKGROUND OF THE INVENTION

A major goal of the Human Genome Project is to provide researchers with an optimal infrastructure for finding and characterizing new genes. The availability of genetic and physical maps of the human genome may greatly accelerate the identification of human genes, including disease genes, and allow subsequent characterization of these genes. Once the genome maps and consensus sequences are obtained, the ability to assess individual variation may open the way to gene discovery and gene diagnosis. Such gene discovery programs may lead to new insights into the organization and functioning of the human genome and its role in the etiology of disease, providing new and highly accurate diagnostic and prognostic tests. Ultimately, the availability of filly characterized genes encoding a variety of functions may provide the raw materials for novel gene therapies and rational drug discovery/design. Other benefits may be recognized.

Rapid and accurate identification of DNA sequence heterogeneity has been recognized as being of major importance in disease management. Comprehensive testing for gene mutational differences can provide diagnostic and prognostic information, which, in the context of integrated relational databases, could offer the opportunity for individualized, more effective health care. Practical examples include current attempts to initiate pre-symptomatic testing programs by looking for mutations in genes predisposing to common diseases such as breast and colon cancer.

A recent estimate for single-nucleotide polymorphism (SNP) due to single-base substitution in the genome approximates 1 SNP/1000 bp. Other types of SNP involve insertion and deletion and are found to occur at $\sim\frac{1}{12}$ kb. Thus far, nucleotide sequencing remains the gold standard for accurate detection and identification of mutational differences. However, large-scale DNA sequencing to detect mutations is not efficient because of the low frequency of SNP. Furthermore, the high costs involved in sequencing have prompted the development of a large number of potentially more cost-effective, alternative, pre-screening techniques. These include single-stranded conformation polymorphism (SSCP) and SSCP-derived methods, chemical or enzymatic mismatch cleavage, denaturing gradient gel electrophoresis (DGGE), matrix-assisted laser desorption/ionization mass spectrometry, 5'nuclease assay, single nucleotide primer extension, and chip-based oligonucleotide arrays, among others.

Two-dimensional (2-D) gel electrophoresis is a commonly used technique for separating proteins based on molecular weight and isoelectric point. This technique is also used for separating DNA molecules based on size and base-pair sequence for detecting mutations or SNPs. The 2-D format for DNA separation increases the number of target fragments that can be analyzed simultaneously.

2-D DNA gel electrophoresis has been used to two-dimensionally resolve the entire E. coli genome and detect differences. DNA fragments can be resolved in two dimensions based on their differences in size and sequence. Sequence-dependent separation is typically achieved in the second dimension using DGGE. Apart from nucleotide sequencing, DGGE is the only known method which offers virtually 100% theoretical sensitivity for mutation detection. Provided the sequence of the fragment of interest is known, DGGE can be simulated on the basis of the melting theory using a computer algorithm. By attaching a GC-rich fragment to one of the PCR (Polymerase Chain Reaction) primers, the target fragment can be designed so that it will always be the lowest melting domain, providing absolute sensitivity to all kinds of mutations.

It is known to combine 2-D DNA gel electrophoresis with extensive PCR multiplexing to produce a high resolution system known as a two-dimensional gene scanning (TDGS) system. TDGS systems can be used for detecting mutational variants in multiple genes in parallel. The resolving power of TDGS has been demonstrated for several large human disease genes, including CFTR (cystic fibrosis transmembrane regulator gene), RB1 (retinoblastoma tumor suppressor gene), MLH1 (MutL protein homolog 1), TP53 (p53 tumor suppressor gene), BRCA1 (breast and ovarian cancer susceptibility gene 1), and TSC1 (tuberous sclerosis complex gene 1), as well as for a part of the mitochondrial genome.

To be suitable for true large-scale analysis, including for example, analysis of essentially all human genes in population-based studies, a mutation scanning system should not only be accurate but also capable of operating at a high throughput in a cost-effective manner. At present, 2-D DNA gel electrophoresis is relatively cost-effective in comparison with other mutation detection techniques. However, TDGS suffers from the fact that it is not a high-throughput platform for large-scale DNA analysis. Despite the selectivity and sensitivity of conventional 2-D DNA analysis, this technique as practiced today is a collection of manually intensive and time-consuming tasks, prone to irreproducibility and poor quantitative accuracy.

Microfluidic systems generally are known and are convenient for performing high-throughput bioassays and bioanalyses. One problem with existing systems is the materials and fabrication procedures used in existing commercial microfluidic devices. Currently, the majority of devices are made from glass or silicon. These materials are often chosen, not because of their suitability for the applications at hand, but rather because the technology is readily transferable from established procedures. A limitation with glass or silicon-based microfluidic devices is the high cost of fabrication and the brittleness of the material.

Separations by DGGE are based on the fact that the electrophoretic mobility of a partially melted DNA molecule is greatly reduced compared to an unmelted molecule. When a mixture of molecules, differing by single base changes, is separated by electrophoresis under partially denaturing conditions, they display different states of equilibrium between the unmelted DNA fragment and the partially melted form. The fraction of time spent by the DNA molecules in the slower, partially melted form varies among specific sequences. Less stable species move more slowly than the more stable ones in an electric field, resulting in efficient separation.

The generation of a temperature gradient in a capillary via ohmic heat produced by a voltage ramp over time is known, as is the use of DGGE in capillary electrophoresis. While these results have some favorable aspects, constructing the gradients is not quite straightforward, particularly for the development of multiple-capillary arrays. Others have demonstrated a 96-capillary array electrophoresis system for screening SNP by surrounding the capillaries with thermal conductive paste and controlling the temporal temperature gradient through the use of an external heating plate. Various drawbacks exist with these approaches.

Another problem with microfluidic devices for 2-D DNA gel electrophoresis is the lack of convenient, effective methodology to transfer DNA molecules from a first dimension to a second dimension after separation of molecules in the first dimension. Microfluidic devices for 2-D DNA gel electrophoresis also suffers from the lack of a convenient method or device for high throughput and high resolution second dimension separation. Current approaches using DGGE or other currently available gel based methods for this sequence-dependent separation in microfluidic devices have limitations in handling for high throughput purposes.

These and other drawbacks exist with known systems and methods.

SUMMARY OF THE INVENTION

One object of the invention is to overcome these and other drawbacks in existing systems and methods.

One embodiment of the invention relates to a microfluidic apparatus for performing 2-D biomolecular separations. According to one aspect of the invention, after a first dimension separation in a first microchannel, the sample material is electrokinetically and simultaneously transferred to an array of microchannels in the second dimension (e.g., by changing the electric potentials at the reservoirs connected to the microchannels). Preferably any separation accomplished in the first dimension is completely retained upon transfer to the second dimension. According to another aspect of the invention, the separation in the second dimension is performed using a temperature gradient (e.g., a spatial or temporal temperature gradient). According to one embodiment of the invention, the biomolecular material comprises DNA and the first dimension separation is a sized-based separation and the second dimension separation is a sequence-based separation.

According to another aspect of the invention, to automate and increase the throughput of 2-D DNA gel electrophoresis, a 2-D plastic microfluidic network is provided for rapidly and accurately resolving DNA fragments based on their differences in size and sequence. The first dimension size-based separation may be performed in a known manner. Instead of continuously sampling DNA analytes eluted from the first size-separation dimension, one aspect of the invention relates to electrokinetically and simultaneously transferring the size-separated DNA fragments from the first dimension (e.g., a microchannel extending from left to right and connecting first and second reservoirs) to a microchannel array between third (and in some embodiments) and fourth reservoirs for performing a sequence-dependent separation. Preferably, the electrokinetic transfer occurs simultaneously in each of the second dimension microchannels. Increased throughput can be achieved by rapid size-based separations (e.g., in the range of 0–200 seconds) followed by simultaneous transfer of size-separated DNA fragments together with parallel sequence-dependent separations in the second dimension. This simultaneous transfer approach also significantly simplifies the procedures compared to those involved in continuous sampling and separation of the eluants from the first dimension.

According to another aspect of the invention, instead of using denaturing reagents such as urea and formamide, DNA fragments (or other materials) in the second dimension are resolved by using a temporal or a spatial temperature gradient. Since the "melting" of DNA fragments is a function of base sequence with GC-rich regions being more stable than AT-rich regions, sequence differences between fragments may be revealed as migration differences. Thus, the invention provides an automated, cost-effective, high throughput, rapid, and reproducible 2-D microfluidic gene scanner. Ultrasensitive measurements of these DNA fragments may then be achieved with an integrated optical detection system (e.g., by using laser-induced fluorescence detection (LIFD) with the addition of intercalating dyes such as ethidium bromide and thiazole orange in the electrophoresis buffer). This 2-D DNA separation platform can perform effectively with even minute DNA samples and enables automation and true system integration of size and sequence-dependent separations with real time fluorescence detection and imaging.

According to one embodiment, the second dimension transfer and the second dimension separation may occur by applying an electric field along the length of the one or more second-dimension microchannels while applying a temperature gradient, thereby denaturing the biomolecules and further separating the biomolecules based on their migration time through the gel contained therein.

According to some embodiments of the invention, various combinations and configurations of microchannels and reservoirs may be implemented to control intersection voltages and enable advantageous separation techniques. For example, in addition to first and second dimension microchannels, other microchannels (e.g., tertiary) may be implemented to enable advantageous separation techniques. Likewise, voltage control microchannels may be implemented to enable advantageous manipulation of samples. In addition, other reservoirs, grouping of microchannels (e.g., parallel groups feeding into respective reservoirs, multiple groups feeding into single, common microchannels, etc.) resistive elements and other configurations may enable advantageous sample separation and manipulation.

According to one embodiment a spatial temperature gradient is formed along the length of the one or more second-dimension microchannels. According to another embodiment, a temporal gradient is used. The temporal or spatial temperature gradient may be created using a variety of techniques including internal and external heat sources. One aspect of the invention relates to 2-D microfluidic networks formed in plastic substrates (e.g., using template imprinting technologies) and integration of this technology with the computerized design of PCR primers that generate a large number of DGGE-optimized target fragments in one single reaction, i.e. a PCR multiplex. The combination of the high throughput and cost-effective 2-D microfluidic gene scanner with the principle of the PCR multiplex may enable an extensive parallel gene scanner for mutation detection in large human disease genes, for exploring human genetic variability in population-based studies, and for other purposes. This may facilitate genome typing of human individuals, comprehensive mutation analysis, and other advantages.

Direct detection of all possible DNA variations at high accuracy in a cost-effective manner will allow for the identification of all possible variants of the multiple genes determining disease susceptibility, disease progression, and response to therapy (pharmacogenomics).

These and other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION

Figure 1:
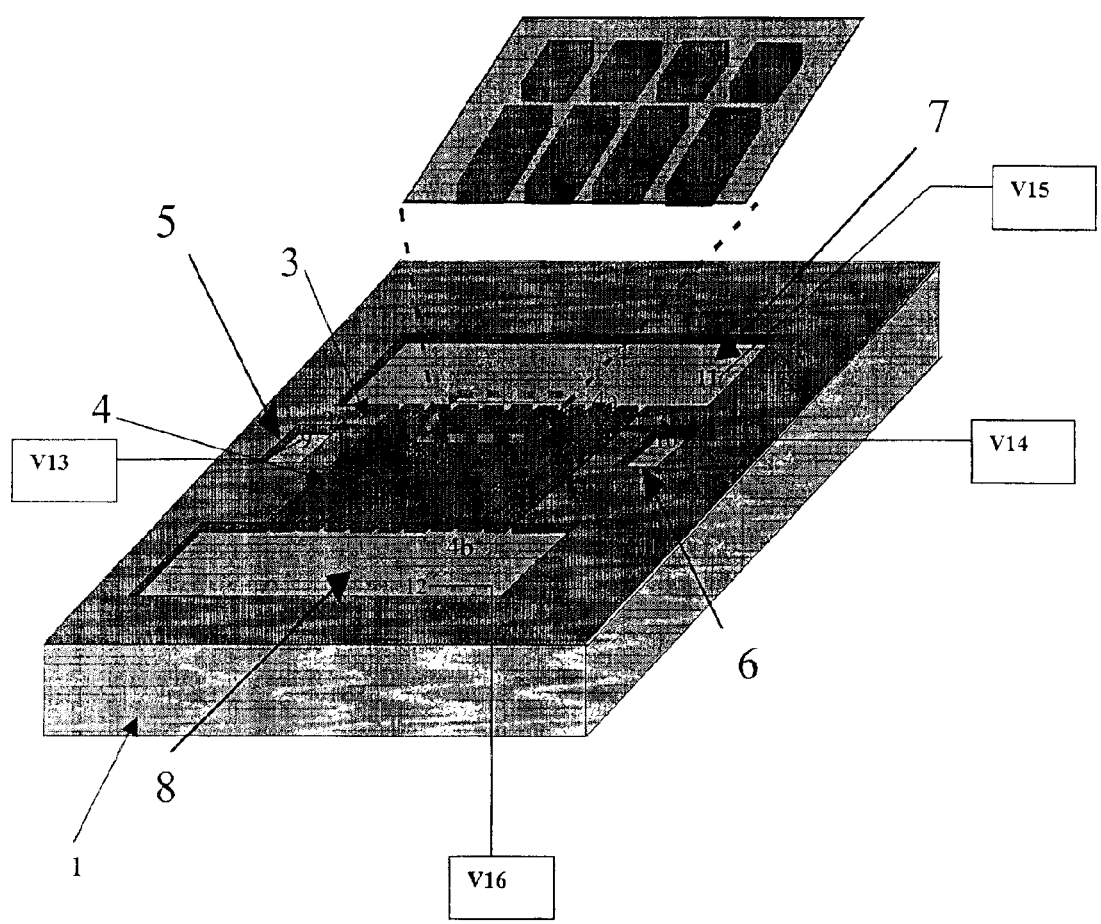
FIG. 1 is a schematic of a microfluidic apparatus according to one embodiment of the invention.

According to an embodiment of the invention illustrated in FIG. 1, a microfluidic 2-D gel electrophoresis apparatus is provided. Microfluidic 2-D gel electrophoresis apparatus may comprise a first planar substrate 1 containing one or more first-dimension microchannels 3 for first dimension separation, as well as a second planar substrate 2 (bonded to first planar substrate 1) to provide enclosure for one or more second-dimension microchannels 4 for second dimension separation.

According to one embodiment, the first-dimension microchannel 3 may extend in a first direction, while an array of one or more second-dimension microchannels 4 may extend from, or intersect with, the first-dimension microchannel 3 in a second direction. Preferably the second direction is orthogonal to the first direction. The first-dimension microchannel 3 may have a first end 3a and a second end 3b. Similarly, an array of one or more second-dimension microchannels 4 may each have a first end 4a and a second end 4b.

According to one embodiment the first end 4a of the one or more second-dimension microchannels 4 may intersect the first-dimension microchannel 3 at various locations along the length of the first dimension microchannel.

According to one embodiment, as illustrated in FIG. 1, the apparatus may further comprise one or more reservoirs (5, 6, 7, 8) and voltage sources (V13, V14, V15, V16) associated with each of the reservoirs, respectively. For example, a first reservoir 5 may be in fluid communication with a first end 3a of the first microchannel 3, and a second reservoir 6 may be in fluid communication with a second end 3b of the first microchannel 3. Additionally, a third reservoir 7 may be in fluid communication with a first end 4a of each of the second dimension microchannels 4, and a fourth reservoir 8 may be in fluid communication with a second end 4b of the second dimension microchannels 4. In other embodiments, some of which are described herein, different configurations of microchannels and reservoirs may be used. Not all embodiments may use four reservoirs. More or less may be used.

Figure 4:
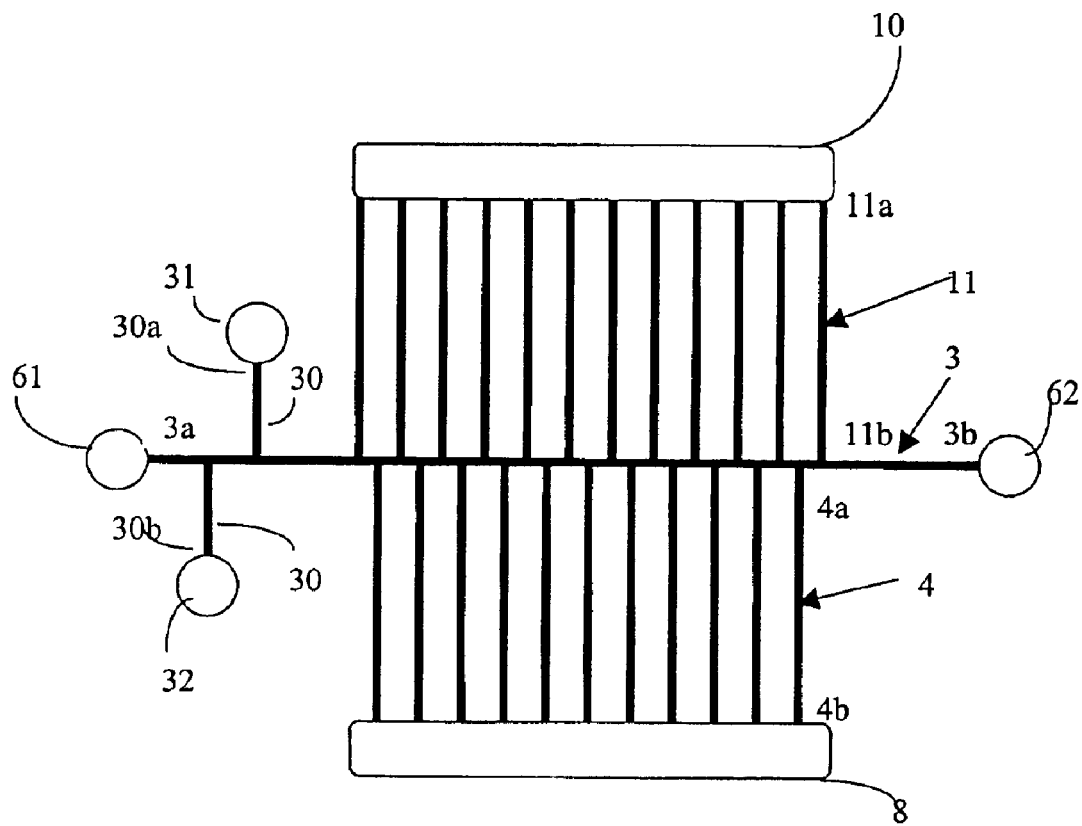
FIG. 4 is a schematic of a microfluidic apparatus with tertiary microchannels according to one embodiment of the invention.

According to one embodiment of the invention, the apparatus may further comprise one or more injection microchannels 30 (as illustrated in FIG. 4), wherein the injection microchannels have a first end 30a and a second end 30b, and wherein the one or more injection microchannels 30 intersect the first-dimension microchannel 3 near the first end 3a of the first-dimension microchannel 3. According to another embodiment, the apparatus may further comprise a sample injection inlet reservoir 31 intersecting the first end 30a of the injection microchannel 30, a sample injection outlet reservoir 32 intersecting the second end 30b of the injection microchannel 30, a first-dimension separation inlet reservoir 61 intersecting the first end 3a of a first-dimension microchannel 3 and a first-dimension separation outlet reservoir 62 intersecting a second end 3b of a first-dimension microchannel 3. As shown in FIG. 1, one or more second-dimension separation inlet reservoirs (e.g. reservoir 7) may intersect a first end 4a of the one or more second-dimension microchannels 4, and one or more second-dimension separation outlet reservoirs (e.g., reservoir 8) may intersect a second end 4b of the one or more second-dimension microchannels 4.

According to one embodiment of the invention, the one or more reservoirs (5–8, 61, 62) may be formed in the first 1 or second 2 substrate, and a plurality of separation electrodes (9, 10, 11, 12) may be provided. A first end (indicated schematically) of separation electrodes (9–12) may be located in communication with the reservoirs 5–8, respectively. A second end (indicated schematically) of the separation electrodes 9–12 may be attached to one or more voltage sources (V13, V14, V15, V16). Likewise, one or more of electrodes (9–12) may also be connected to ground potential (e.g., ~0 Volts).

As illustrated in FIG. 1, the device may comprise one or more inlet reservoirs (e.g. reservoir 5) and outlet reservoirs (e.g. reservoir 6) at the ends (3a, 3b) of the first microchannel 3, and one or more inlet reservoirs (e.g. reservoir 7) and one or more outlet reservoirs (e.g. reservoir 8) at the ends (4a, 4b) of the second dimension microchannels 4. Other configurations may be used. For example, in one embodiment, the second ends 4b of the one or more second dimension microchannels 4 may terminate at one or more points between the first and second ends (3a, 3b) of the first dimension microchannel 3. In such embodiments, no second dimension inlet reservoir may be provided.

In another embodiment, shown, for example in FIG. 4, one or more second-dimension separation outlet reservoirs 8 may intersect the second end 4b of the one or more second-dimension microchannels 4, and one or more tertiary inlet reservoirs 10 may intersect the first end 11a of the one or more tertiary microchannels 11. The second end 11b of the one or more tertiary microchannels 11 may terminate at one or more points between the first 3a and second 3b ends of the first dimension microchannel 3, and the first ends 4a of the one or more second dimension microchannels 4 may terminate at one or more points between the first and second ends 3a, 3b of the first dimension microchannel 3. In this embodiment, the one or more points at which the second ends (4b) of the tertiary microchannels 11 and second dimension microchannels 4 terminate at the first dimension microchannel 3 may be staggered. Preferably, the number of tertiary microchannels 11 is equal to one more than the number of secondary microchannels 4, and the one or more points at which the first ends 4a of the second dimension microchannels 4 terminate at the first dimension microchannel 3 are staggered from the one or more points at which the second ends 11b of the tertiary microchannels 11 terminate at the first dimension microchannel 3 by half the distance between adjacent tertiary microchannels 11. In this embodiment, the one or more second dimension separation inlet reservoirs may be omitted.

According to one embodiment, reservoirs (e.g., reservoirs 5, 6, 7, 8) may be filled with an electrolyte solution. The electrolyte solution may include a buffer (e.g, an electrophoresis buffer, or a salt solution). In some embodiments, the electrolyte solution may contain 1×TBE buffer (89 mM Tris, 89 mM boric acid, 2 mM EDTA). The electrolyte solution may also have a pH over a broad range of pH values, with a preferred pH ranging between 6 and 10, or more preferably with a pH of about 8–9.

In one embodiment, the grounding and separation electrodes may be formed from any suitable thin film metal deposited and patterned onto the first 1 and second 2 planar substrate. Additionally, the temporal or spatial temperature gradient may be created using a variety of techniques including internal and external heat sources.

Figure 2A:
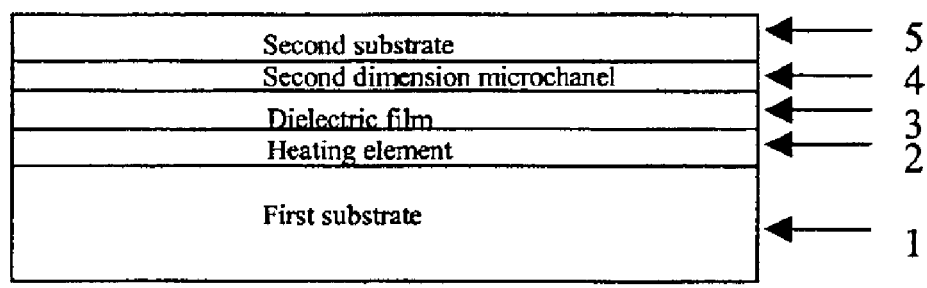
FIG. 2A is a side view of a microfluidic apparatus according to one embodiment of the invention.
Figure 2B:
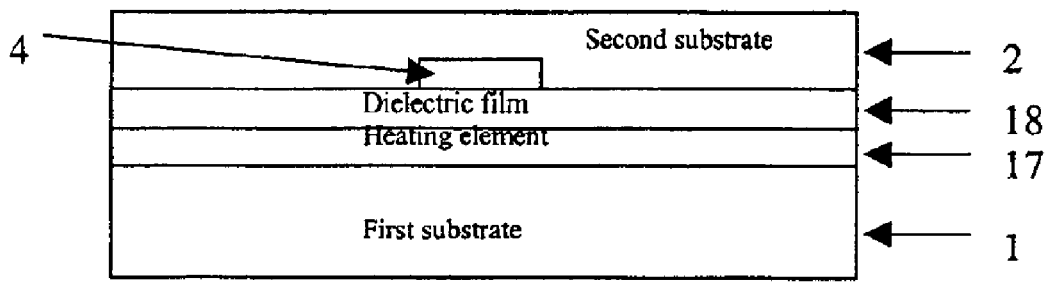
FIG. 2B is a front sectional view of a microfluidic apparatus according to one embodiment of the invention.

According to one embodiment of the invention, one or more heating elements 17 may be affixed to an exposed outer surface of the first 1 or second 2 planar substrate for controlling the temperature of the substrates. According to another embodiment of the invention, as illustrated in FIGS. 2A, 2B, one or more heating elements 17 may be bonded between (or otherwise integrated with) the first 1 and second 2 planar substrates. A nonconducting dielectric film 18 may also be placed between the heating elements 17 and the second planar substrate 2 containing one or more microchannels. The one or more heating elements 17 may be shaped to provide a desired temperature distribution across the planar substrate (1, 2) when current is passed through the one or more heating elements 17. In some embodiments, the temperature gradient may comprise a temporal temperature gradient, wherein the one or more heating elements 17 may induce a constant spatial temperature across the entire length and width of the one or more second-dimension microchannels 4, and wherein the constant spatial temperature is varied with time. In other embodiments, a linear spatial temperature profile may be imposed along the length of the one or more second-dimension microchannels 4.

Resistive heating of the one or more heating elements 17 may be used to produce the desired temperature gradient. The heating elements may be made from any suitable material. Platinum may, for example, be used as a preferred heating element 17 material for imposing temperature gradient along microchannels. By using platinum heating elements 17, the local temperature may be monitored by measuring changes in resistance. Platinum may be replaced with other less expensive electrode materials with acceptable temperature coefficients of resistance including, for example, thin film gold, metal foil, conductive polymer(s), conductive ink, electrically-conductive wire, or other materials. Other temperature control structures and techniques may be used.

The spatial temperature gradient may vary from about 20–25° C. at the intersection between the first dimension microchannel 3 and the one or more second-dimension microchannel 4, to about 70–90° C. at the second end 4b of the one or more second-dimension microchannels 4. Alternatively, the spatial temperature gradient may vary from about 70–90° C. at the intersection between the first dimension microchannel 3 and the one or more second-dimension microchannel 4, to about 20–25° C. at the second end 4b of the one or more second-dimension microchannels 4. The spatial temperature gradient may be replaced by a temporal temperature gradient where the one or more heating elements 17 induces a constant spatial temperature across the entire length and width of the one or more second-dimension microchannel 4 and the constant spatial temperature is varied with time. The constant spatial temperature may be varied from an initial temperature of about 20–25° C. to a final temperature of about 70–90° C. Alternatively, the constant spatial temperature may be varied from an initial temperature of about 70–90° C. to a final temperature of about 20–25° C.

In some embodiments, microchannels (e.g. 3, 4) may have depth to width ratio of approximately 1:3. Other ratios and dimensions may be used. For example, microchannels with an average depth of 10 μm may have an average width of 30 μm. However, both depth and width preferably range from 5 to 200 μm. For illustrative purpose, the width mentioned herein is from trapezoidal shaped microchannel cross-sections. Other shapes for microchannel cross-sections may be used, for example rectangular, circular, or semi-circular cross-sections. The microchannels (e.g. 3, 4) can be any suitable length. A preferred length ranges from about 1 to about 10 cm. Other lengths may be used. Some embodiments may have other microchannel dimensions for various applications.

The number of microchannels (e.g. 3, 4, 11) and the spacing therebetween, may be application dependent. The spacing between the second dimension microchannels 4 in the array may determine the size of the sample plug being introduced from the first to the second dimensions. The extent of resolution loss during the transfer step is in part dependent upon the spacing and the DNA bandwidth achieved from size-based separation in the first dimension. Minimal resolution loss may be achieved as there may be no mixing during the electrokinetic transfer of DNA fragments. The number second dimension of microchannels in the array may also range from 10 to 1000, or more.

Separation efficiency and resolution of DNA fragments may be dependent upon the size-sieving polymer characteristics and the applied electric potential. According to one aspect of the invention, a preferred separation media for electrophoresis in microchannels (e.g. 3, 4) is 1×TBE buffer (89 mM Tris, 89 mM boric acid, 2 mM EDTA) containing 2% poly(ethylene oxide) (PEO). It should be noted that microchannels (e.g. 3, 4) may be filled with any other polymeric media for separating DNA, protein, other biomolecules and chemical composites.

According to one embodiment of the invention, a voltage source (V13, V14, V15, V16) may be attached to a second end (indicated schematically) of a selected number of the one or more separation electrodes (indicated schematically). Due to the extremely large surface area to volume ratio of microchannels for efficient heat dissipation, the application of an electric field may enable rapid and excellent separation of DNA fragments in a microfluidic network. A preferred electric field for separating DNA fragments in the present invention range from 100–1000 V/cm, however, other electric field strengths may be used.

Various methods of operation may be implemented consistent with the objectives of the invention. According to one embodiment, as illustrated in FIG. 4, a method of operation of the invention may include performing two-dimensional gel electrophoresis of biomolecules by applying a suitable electric field along the length of an injection microchannel 30. A sample stream containing the biomolecules of interest may be injected from the first end 30a of the injection microchannels 30 towards the second end 30b of the injection microchannel 30. A high voltage may be applied to an electrode (not shown) disposed within the injection outlet reservoir 32, while a grounding voltage may be applied to an electrode (not shown) disposed within the injection inlet reservoir 31. All other reservoirs may be disconnected from any voltage source. This arrangement may cause the sample stream to cross through a portion of the first-dimension microchannel 3. By removing the high electric field within the injection microchannel 30 and applying a high electric field along the length of the first-dimension microchannel 3, biomolecules within the sample stream that crosses through the first-dimension microchannel 3 may be separated within the first-dimension microchannel 3 according to their migration time through the gel contained therein. This may result in separation of the biomolecules based on their size. By applying a high voltage to an electrode (not shown) disposed within the first-dimension outlet reservoir (e.g., 6, 62), and by grounding an electrode (not shown) disposed within the first-dimension inlet reservoir (e.g., 5, 61) and disconnecting all other reservoirs from any voltage source, the separated sample stream may pass by the one or more second-dimension microchannels 4 intersecting with the first-dimension microchannels 3. The first-dimension separation may be performed within the first-dimension microchannel 3 before transferring the separated sample stream past the one or more second-dimension microchannels 4 intersecting with the first-dimension microchannels 3, or first-dimension separation may be performed during this transfer process.

According to an embodiment of the invention, further separation and denaturing of the biomolecules may occur through the application of an electric field along the length of the one or more second-dimension microchannels 4, while simultaneously applying a temperature gradient.

According to one embodiment, a spatial temperature gradient may be formed along the length of the one or more second-dimension microchannels 4. A voltage may be applied to an electrode (not shown) disposed within the second-dimension outlet reservoir 8, and a grounding voltage may be applied to the electrode disposed within the second-dimension inlet reservoir 7. Each of the remaining reservoirs may be disconnected from any voltage source.

Figure 3:
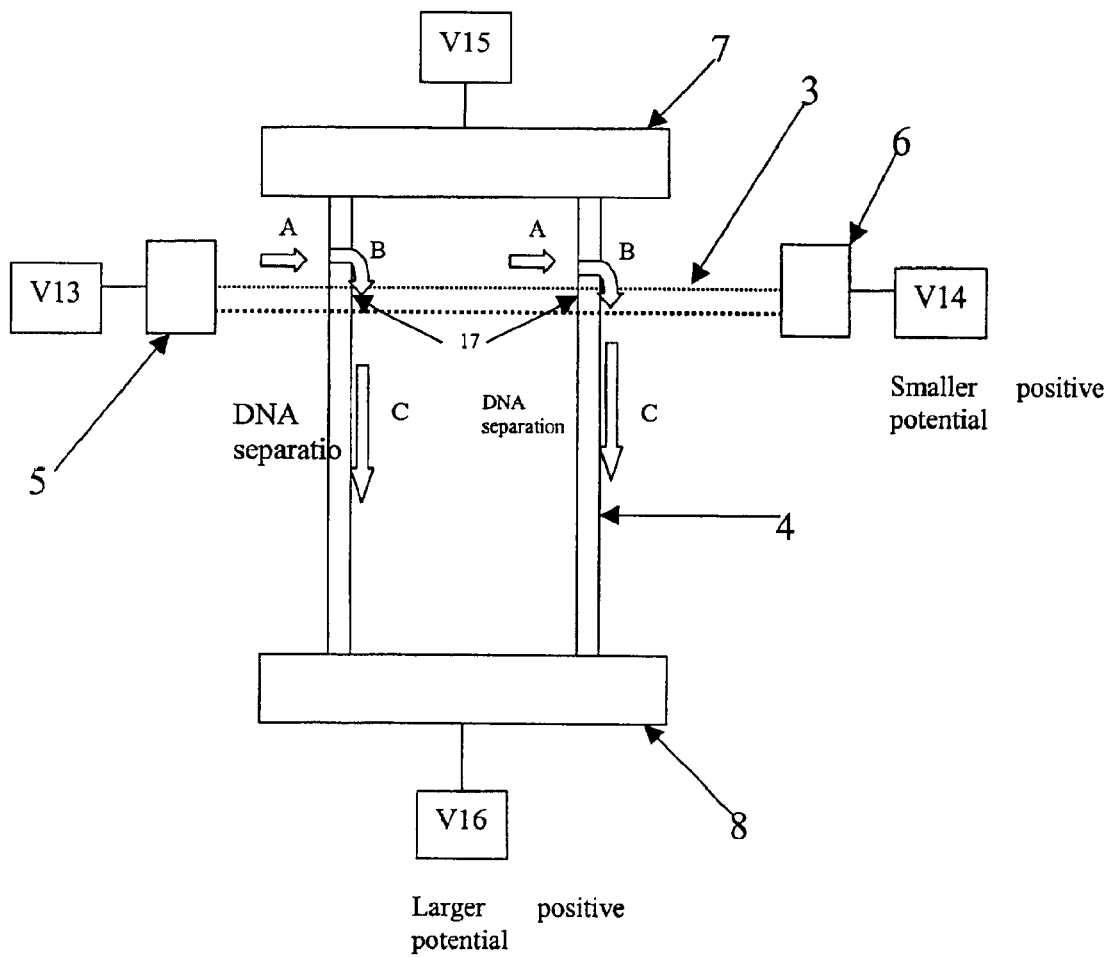
FIG. 3 illustrates electrokinetic transfer of DNA from first dimension to second dimension according to one embodiment of the invention.

According to one embodiment of the invention, as illustrated in FIG. 3, a relatively low voltage may be applied to the first-dimension outlet reservoir 6, while a grounding voltage may be applied to the first-dimension inlet reservoir 5. The one or more second-dimension inlet reservoirs 7 may be disconnected from any voltage source. Pursuant to this arrangement, when a relatively high electric field is applied along the length of the one or more second-dimension separation microchannels 4, a small electric field may be simultaneously generated along the length of the first-dimension microchannel 3, thereby causing biomolecules to be drawn slightly towards the first-dimension dimension outlet reservoir to ensure efficient transfer of the biomolecules from the first-dimension microchannel into the one or more second dimension microchannels 4.

According to one embodiment of the invention, as illustrated in FIG. 4, a grounding voltage may be applied to the one or more tertiary reservoirs 10, while a high voltage may be applied to the one or more second-dimension outlet reservoirs 8. All other reservoirs may be disconnected from any voltage source. Pursuant to this arrangement, a high electric field is applied along the length of the one or more second-dimension separation microchannels 4, with said electric field passing from the one or more tertiary microchannels 11 through the one or more regions of the first-dimension microchannel 3 between adjacent tertiary 11 and second-dimension microchannels 4, and into the one or more second-dimension microchannels 4, thereby causing biomolecules within the first-dimension microchannel 3 to be drawn into the one or more second-dimension microchannels 4 to ensure efficient transfer of the biomolecules from the first-dimension microchannel 3 into the one or more second dimension microchannels 4.

According to another aspect of the invention, one or more intersection control voltages may be applied to the one or more second-dimension separation outlet reservoirs 8 or tertiary inlet reservoirs 10, as illustrated in FIG. 4, and the one or more second-dimension separation inlet reservoirs 7 (see FIG. 1). This may control the electric field lines at the intersection of the one or more first-dimension separation microchannels 3 and the one or more second-dimension separation microchannels 4 in such a manner that the distribution of biomolecules undergoing separation during the first-dimension separation step are not substantially affected by the intersections.

Figure 5:
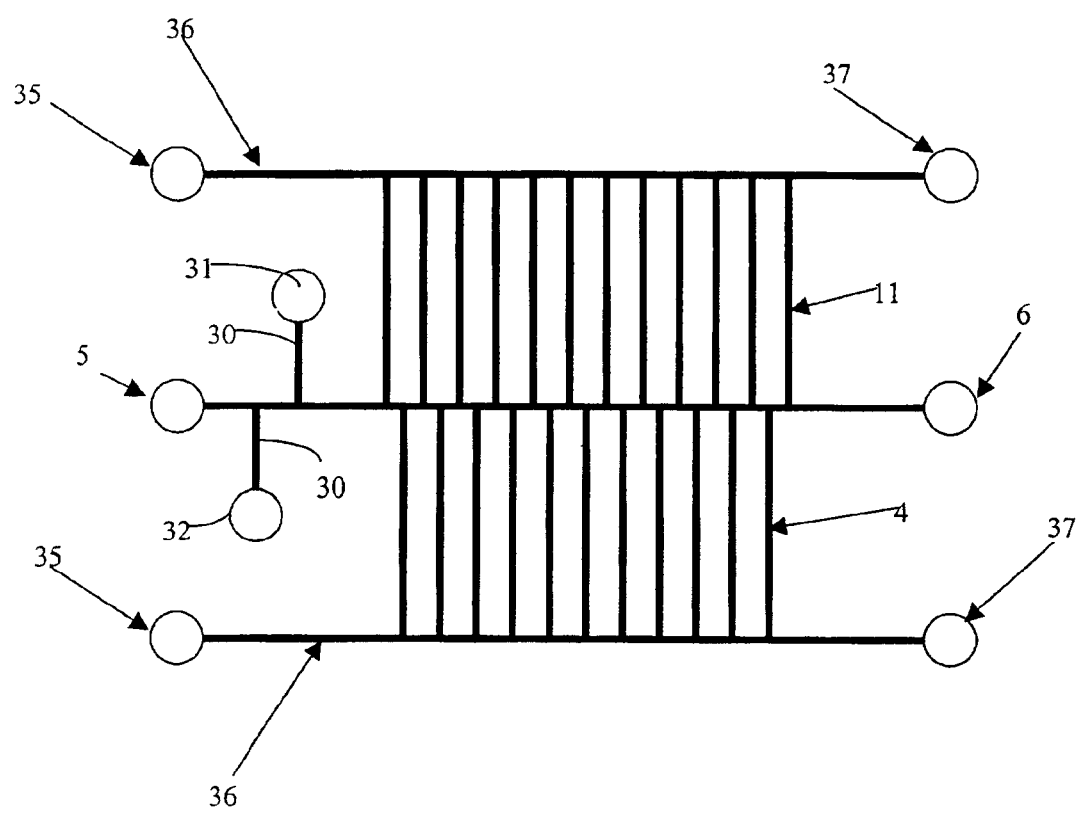
FIG. 5 is a schematic of a microfluidic apparatus with voltage control microchannels according to one embodiment of the invention.

According to an embodiment, as depicted in FIG. 5, the one or more intersection control voltages may be applied using a plurality of voltage sources, wherein one voltage source (35 and 37) may be applied to the one or more inlet reservoirs 35 of the one or more voltage control microchannels 36, and a second voltage source may be connected to the one or more outlet reservoirs 37 of the one or more voltage control microchannels 36 to generate a potential gradient along fluid within the one or more voltage control microchannels 36. The geometry of the one or more voltage control microchannels 36 may be selected such that the intersection control voltage at the one or more intersections of the voltage control microchannels 36 and the second-dimension microchannels 4 and/or tertiary microchannels 11 is set by the voltages applied at the voltage control reservoirs (not shown in the figure). Further, the one or more intersection control voltages may be chosen such that the voltage within the one or more second-dimension microchannels 4 and/or tertiary microchannels 11 near the intersection of the one or more first-dimension separation microchannels 3 and the one or more second-dimension separation microchannels 4 (connected to the reservoir at which the intersection control voltage is applied) is slightly different than the voltage within the intersection itself. In this embodiment, the one or more tertiary inlet reservoirs 10 are omitted.

Figure 6:
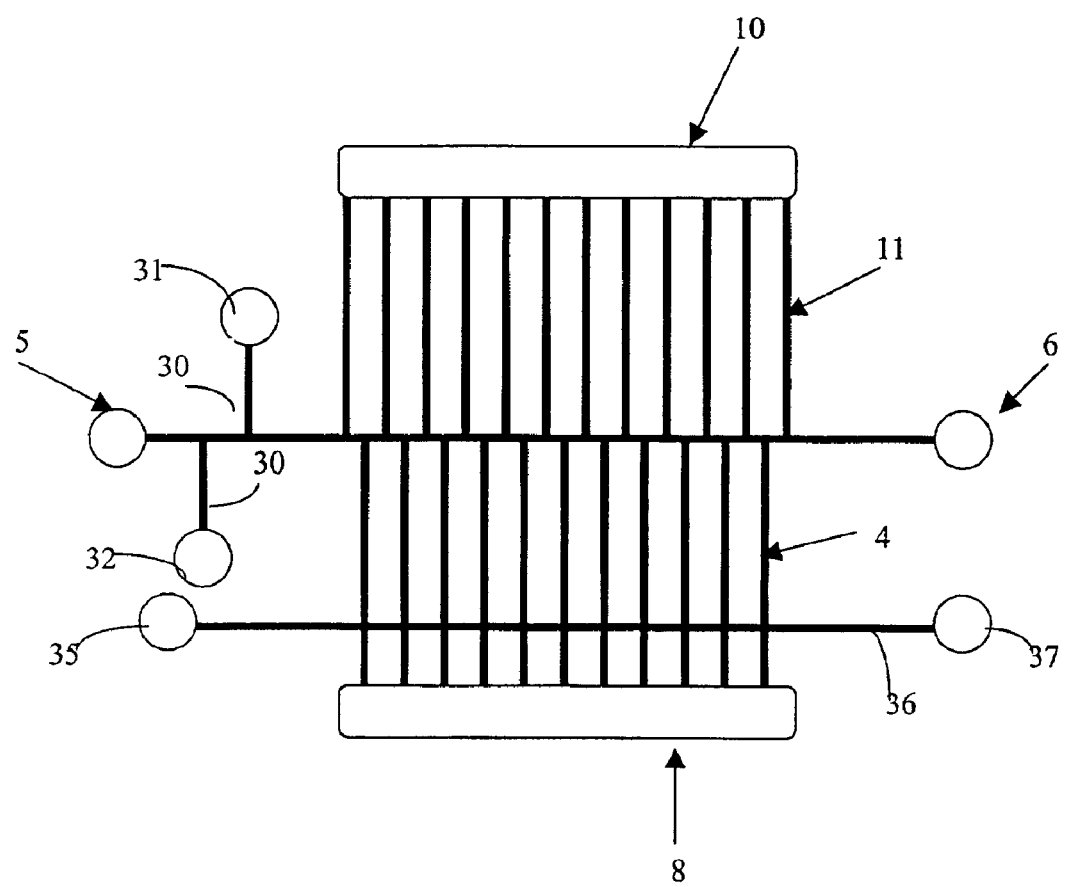
FIG. 6 is a schematic of a microfluidic apparatus comprising a voltage control microchannel combined with second-dimension outlet reservoir according to one embodiment of the invention.

According to another aspect of the invention, depicted in FIG. 6, a single voltage control microchannel 36 may be combined with a second-dimension outlet reservoir 8.

Figure 7:
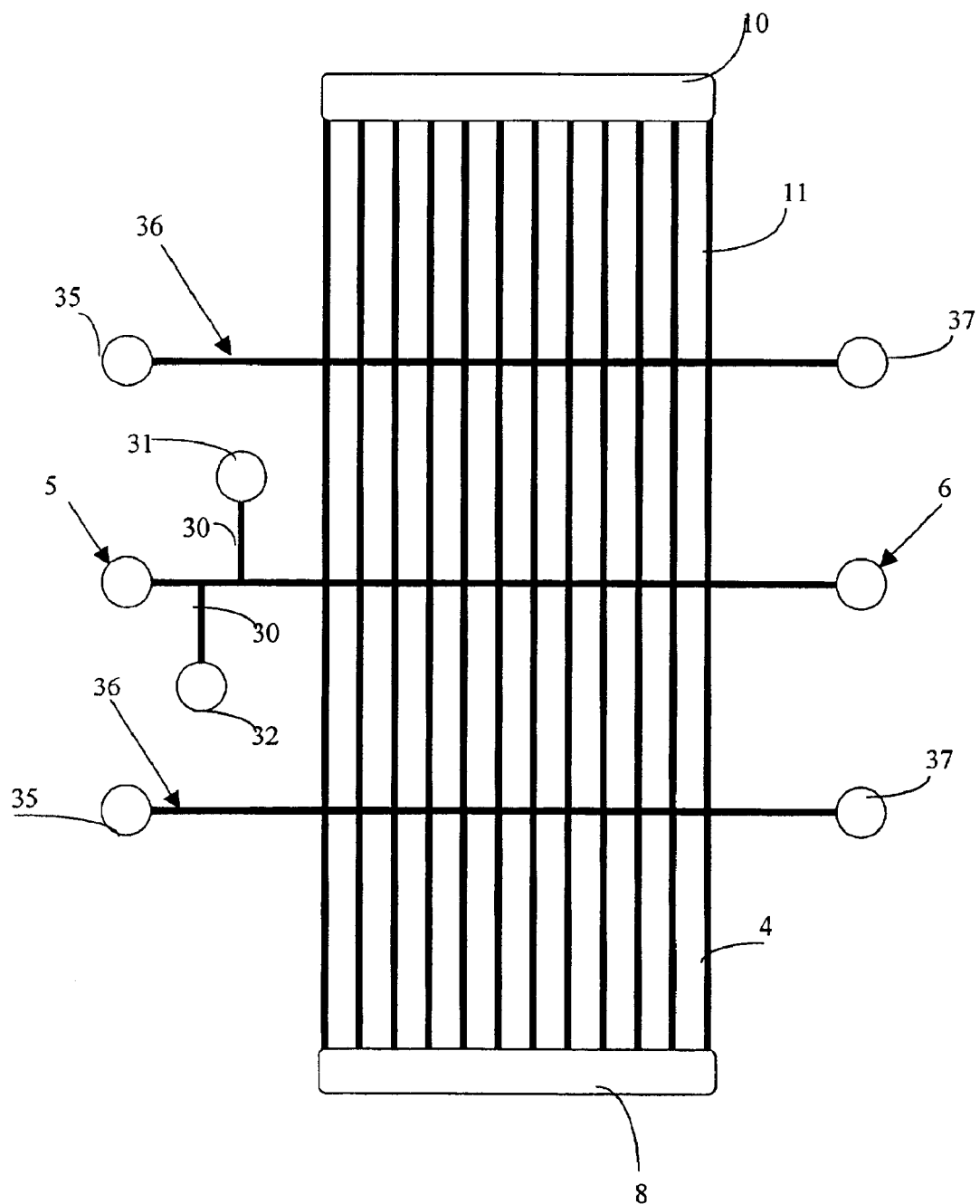
FIG. 7 is a schematic of a microfluidic apparatus showing voltage control microchannels intersecting other microchannels according to one embodiment of the invention.

According to another aspect of the invention, depicted in FIG. 7, one or more voltage control microchannels 36 may intersect the one or more tertiary microchannels 11, and one or more voltage control microchannels 36 may intersect the one or more second-dimension microchannels 4.

Figure 8:
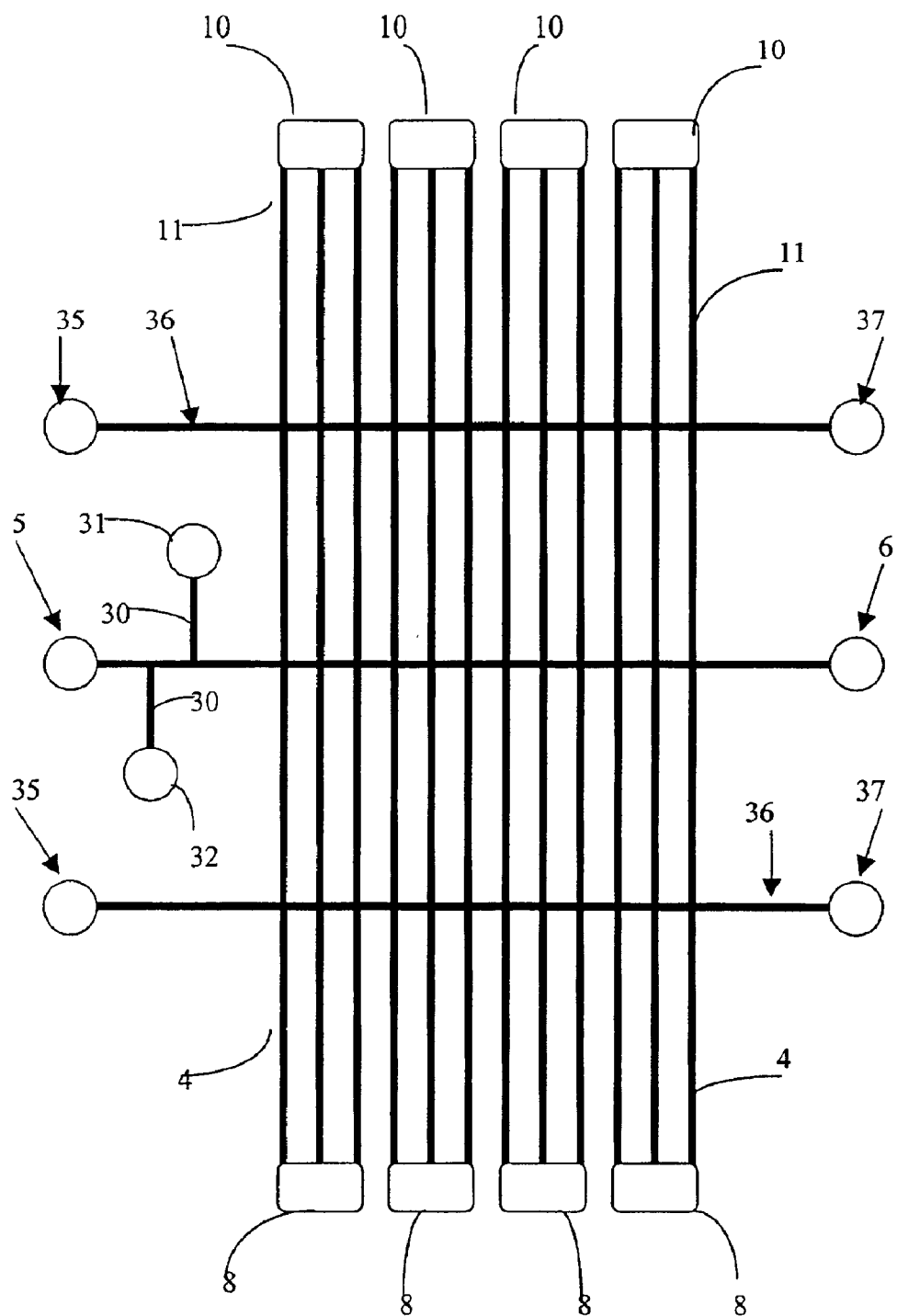
FIG. 8 is a schematic of a microfluidic apparatus showing grouping of tertiary or second-dimension microchannels according to one embodiment of the invention.

According to another aspect of the invention, depicted in FIG. 8, groups of one or more tertiary microchannels 11 may intersect one or more tertiary inlet reservoirs 10. Similarly, groups of one or more second-dimension microchannels 4 may intersect one or more second-dimension outlet reservoirs 8

Figure 9:
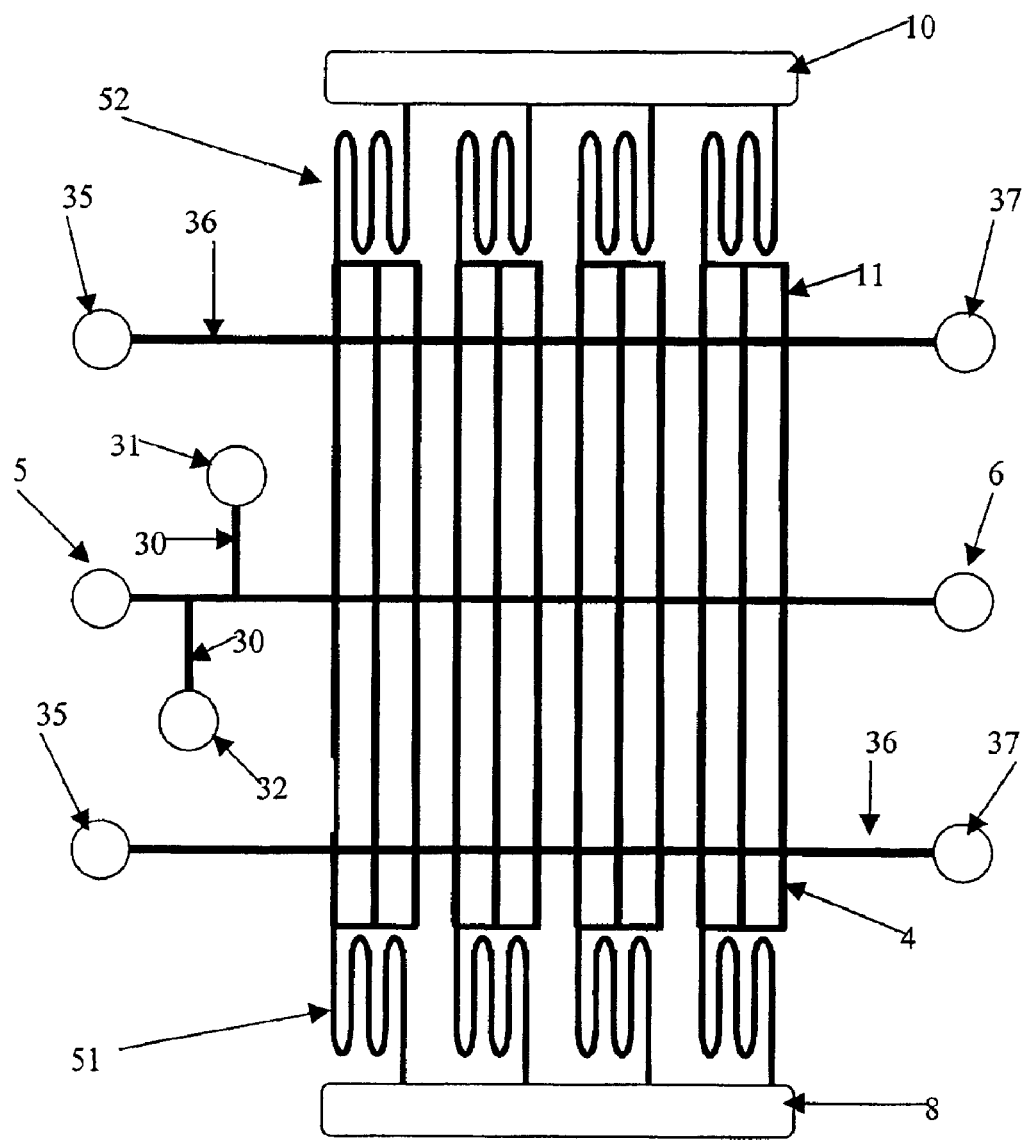
FIG. 9 is a schematic of a microfluidic apparatus showing groups of tertiary or second-dimension microchannels merging into single common microchannels according to one embodiment of the invention.

According to another aspect of the invention, depicted in FIG. 9, groups of one or more tertiary microchannels 11 may merge into a single common tertiary microchannel 52, which intersects the one or more tertiary inlet reservoirs 10. Similarly, groups of one or more second-dimension microchannels 4 may merge into a single common second-dimension microchannel 51, which intersects the one or more second-dimension outlet reservoirs 8.

According to one embodiment, the one or more intersection control voltages may be applied using a plurality of voltage sources, wherein one voltage source may be connected to the first end of a first resistive element, and a second voltage source may be connected to the second end of the first resistive element to generate a potential gradient along the first resistive element. The resistive element may placed in electrical contact with the one or more second-dimension separation inlet reservoirs such that the intersection control voltage in each reservoir is set by the voltage of the first resistive element at the point of electrical contact. Further, the one or more intersection control voltages may be chosen such that the voltage near the intersection of the one or more first-dimension separation microchannels 3 and the one or more second-dimension separation microchannels 4 (connected to the reservoir at which the intersection control voltage is applied) is slightly different than the voltage within the intersection itself.

A third voltage source may be connected to the first end of a second resistive element, and a fourth voltage source may be connected to the second end of the second resistive element to generate a potential gradient along the second resistive element. The second resistive element may then be placed in electrical contact with the one or more second-dimension separation inlet reservoirs, such that the intersection control voltage in each reservoir is set by the voltage of the second resistive element at the point of electrical contact. The one or more intersection control voltages may be chosen such that the voltage near the intersection of the one or more first-dimension separation microchannels 3 and the one or more second-dimension separation microchannels 4 (connected to the reservoir at which the intersection control voltage is applied) is slightly lower than the voltage within the intersection itself.

Figure 10:
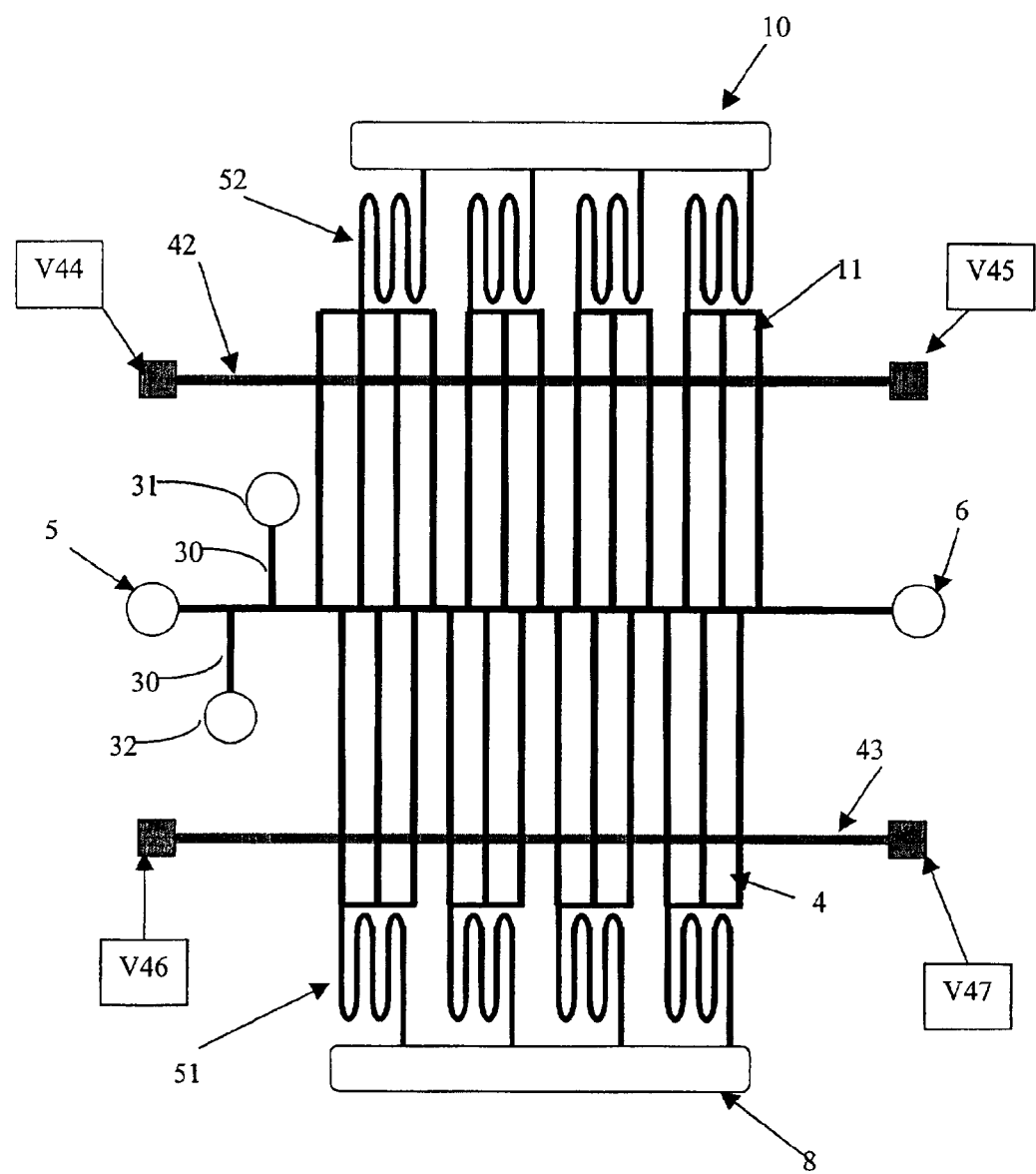
FIG. 10 is a schematic of a microfluidic apparatus showing electrically resistive elements intersecting tertiary or second-dimension microchannels according to one embodiment of the invention.

According to another aspect of the invention, depicted in FIG. 10, one or more electrically-resistive elements (42, 43) such as a thin-film metal, wire, conductive polymer, or similar material may intersect the one or more tertiary microchannels 11 and the one or more second-dimension microchannels 4, with the one or more resistive elements (42, 43) in electrical contact with the fluid within the microchannels. One or more voltage sources (V44, V45, V46, V47) are applied at each end of the one or more resistive elements (42, 43), thereby creating a voltage drop along the length of the resistive elements (42, 43). Since the one or more resistive elements (42, 43) are in electrical contact with the fluid at the points of intersection with the microchannels, the local voltage at each point in the microchannel may be controlled in this manner, with the voltages defined by the one or more voltage sources (V44, V45, V46, V47) and the resistance of the one or more resistive elements (42, 43).

In at least some embodiments of the invention, temperature-gradient gel electrophoresis (TGGE) may be used instead of DGGE. In TGGE, instead of a denaturing gradient along the gel, a spatial or temporal temperature gradient is used to perform the same function. Since the "melting" of DNA fragments is a function of base sequence with GC-rich regions being more stable than AT-rich regions, sequence differences between fragments will be revealed as migration differences. Ultrasensitive measurements of these DNA fragments may be performed by using LIFD with the addition of intercalating dyes such as ethidium bromide and thiazole orange in the electrophoresis buffer. Other optical techniques may be used.

According to one embodiment of the present invention, a method to integrate electrodes into plastic substrates for imposing temperature gradient is provided. Integrating the electrodes directly into the microfluidic device may significantly reduce the overall size and cost of the device. In addition, by heating the fluidic channels directly, the thermal mass associated with external heating elements may be eliminated, resulting in faster thermal time constants, and more rapid, overall separation speeds.

A preferred method of electrode integration may be realized by depositing evaporated and/or sputtered platinum films on a polycarbonate plastic substrate, followed by a lamination of a thin plastic layer atop the metallized plastic to prevent direct contact between the thermal electrodes and separation samples.

In some embodiments, bulk wires and/or foil may be integrated into the plastic substrate using a hot embossing technique. In one embodiment of the invention, the electrodes may be isolated from the separation channels preferably by a thin polydimethylsiloxane (PDMS) or by any laminated plastic layer, to prevent modification of microchannel surface chemistry.

According to one embodiment of the invention, performance of the fabricated microchannel devices with integrated temperature-control electrodes is assessed by coating the topside of the channels with commercially-available microencapsulated thermochromic liquid crystals, which change colors with variations in temperature.

The one or more separation electrodes may include a thin film metal deposited and patterned onto first or second planar substrate.

While the first 1 and second 2 planar substrates made be made from various materials, including, glass or silicon, various advantages may be obtained from the use of plastic, e.g., polycarbonate plastic. One of the advantages of the use of plastic substrates in the present invention is that it may not suffer from the adverse effects of sample leakage at channel junctions caused by diffusion and unwanted electro-osmotic flows. Sample leakage at channel junctions has been one of the problems in microfluidic devices. These leakages are primarily caused by the combined effects of sample diffusion and undesired electroosmotic flows. Plastic substrates used in the present invention are relatively hydrophobic and exhibit smaller electroosmotic flow than silica and others due to their lack of significant surface charge. It should be noted that microfluidic 2-D electrophoresis device can also be made up of glass, silicon or any other combination of dissimilar materials including glass, PDMS, plastic, and silicon.

PDMS may have some particular advantages. PDMS is optically transparent at the wavelengths required for the fluorescence detection of DNA fragments. The low background fluorescence associated with PDMS may offer a better substrate than many other plastic materials for fluorescence detection. In addition, the PDMS substrate containing the microfluidic network is oxidized in an oxygen plasma. The plasma introduces silanol groups (Si—OH) at the expense of methyl groups (Si—CH$_3$). These silanol groups may then condense with appropriate groups (OH, COOH, ketone) on another surface when the two PDMS layers are brought into conformal contact. Oxidized PDMS also seals irreversibly to other materials, including glass, Si, SiO$_2$, quartz, silicon nitride, polyethylene, polystyrene, and glassy carbon. Oxidation of the PDMS has the additional advantage that it renders the surface hydrophilic because of the presence of silanol groups. These negatively charged channels have greater resistance to adsorption of hydrophobic and negatively charged analytes (i.e. DNA fragments) than unmodified PDMS.

Figure 11:
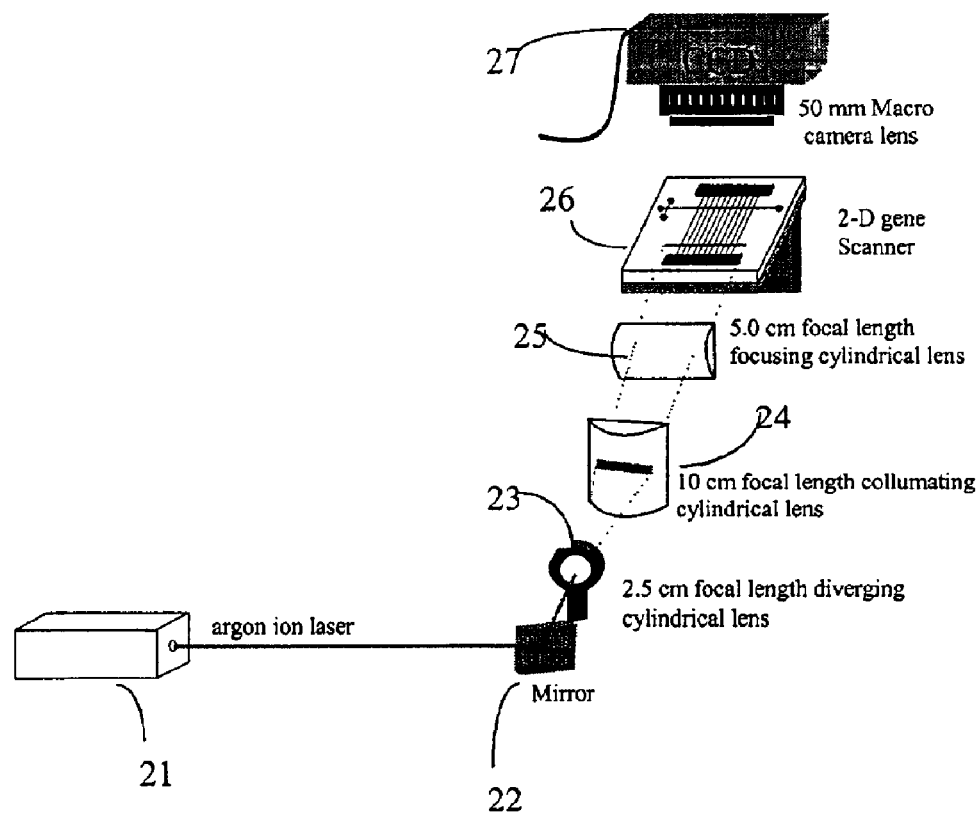
FIG. 11 is a schematic of a laser-induced fluorescence detection setup for line-based fluorescence detection in a second dimension of a microchannel array according to one embodiment of the invention.

One of the objects of the present invention is integration of the 2D microfluidics platform with an ultrasensitive (e.g. LIFD) system for the simultaneous and multi-channel monitoring of DNA fragments near the end of the second-dimension microchannel array. As shown in FIG. 11, excitation of the intercalated ethidium bromide is performed by the argon ion laser 21 (e.g. tuned to 514 nm). One molecule of ethidium bromide, present in the electrophoresis buffer, intercalates at every 4–5 base pairs of double-stranded DNA. Upon intercalation, the quantum yield of ethidium bromide increases 20–30 fold while its fluorescence emission blue-shifts from 604 nm to 590 nm. The output beam from the laser is diverged, collimated to span the entire second dimension microchannel array, and focused vertically in a narrow line across the array. For example, in one embodiment, this is achieved by directing the laser beam (e.g., with a mirror 22) to a (diverging) 2.5 cm focal length plano-concave cylindrical lens 23 in series with a (collimating) 10 cm focal length plano-convex cylindrical lens 24 and a (focusing) 5.0 cm focal length plano convex cylindrical lens 25, respectively. The fluorescence in each channel of the array is independently monitored using a charged-coupled device (CCD) camera 27 with a 50 mm macro Nikon camera lens. The CCD sensor is comprised of 26 $\mu$m pixels positioned in a 1024×128 array. The system is arranged so that a single column of pixels on the sensor is designated to measure the fluorescence intensity emitted from each individual channel over time. A 532 nm rejection band filter (OD>6) is used in series with a 595 nm bandpass emission filter to eliminate laser scatter.

The 2-D DNA separation platform of the present invention may require only minute DNA samples, and may enable automation and true system integration of size and sequence dependent separations with real-time fluorescence detection and imaging.

In some embodiments, microfluidic 2-D DNA gel device of the present invention may be integrated with PCR based multicolor detection system that will allow multiplexing mutation detections for multiple genes by using different dye-labeled primers in a known manner. The techniques in this system may require automated sample preparation for nucleic acid extraction (from blood, tissue, etc.), purification/isolation, amplification, digestion, and tagging.

In some embodiments, the electrokinetic transfer method may be performed to transfer proteins, peptides, and other chemical or biological composites from one dimension to another dimension of a gel electrophoresis device. As used herein, electrokinetic transfer includes a method or a system which transfer materials from a channel and/or chamber containing structure in one dimension, to similar structures in other dimensions, through the application of electric fields to the materials, thereby causing the transfer of the materials.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

We claim:

1. A microfluidic apparatus for performing two-dimensional biomolecular separations, the apparatus comprising:

at least one first dimension microchannel having at least a first surface and a second surface;

an array of second dimension microchannels intersecting the first surface of the at least one first dimension microchannel;

an array of tertiary microchannels intersecting the second surface of the at least one first dimension microchannel means for performing a first biomolecular separation in the at least one first dimension microchannel to produce a separated sample;

means for transferring the separated sample to the microchannels of the array of second dimension microchannels; and means for performing a second separation in the second dimension microchannels, where the second separation is performed by applying a temperature gradient.

2. The apparatus of claim 1 wherein the temperature gradient comprises a spatial temperature gradient.

3. The apparatus of claim 1 wherein the temperature gradient comprises a temporal temperature gradient.

4. The apparatus of claim 1 further comprising internal heating means for producing the temperature gradient.

5. The apparatus of claim 4 wherein the internal heating means comprises electrodes embedded within the apparatus.

6. The apparatus of claim 1 further comprising external heating means for producing the temperature gradient.

7. The apparatus of claim 1 wherein one or more heating elements is affixed to an exposed outer surface of a planar substrate, and by which the temperature of the substrate may be controlled.

8. The apparatus of claim 1 wherein one or more heating elements is bonded between a first and second planar substrates, and wherein the one or more healing elements is shaped to provide a desired temperature distribution across the first and second planar substrates when current is passed through the one or more heating elements.

9. The apparatus of claim 8 wherein the one or more heating elements comprises thin film gold.

10. The apparatus of claim 8 wherein the one or more heating elements comprise metal foil.

11. The apparatus of claim 8 wherein the one or more heating elements comprise conductive polymer.

12. The apparatus of claim 8 wherein the one or more heating elements comprise conductive ink.

13. The apparatus of claim 8 wherein the one or more heating elements comprise an electrically-conductive wire.

14. The apparatus of claim 1 wherein a nonconducting dielectric film is located between a heating element and a second planar substrate containing one or more of the second dimension microchannels.

15. The apparatus of claim 1 further comprising one or more separation electrodes wherein the one or more separation electrodes comprise a thin film metal deposited and patterned onto a planar substrate.

16. The apparatus of claim 1 further comprising one or more separation electrodes wherein the one or more separation electrodes comprise electrically-conductive wires positioned between a first and second planar substrates.

17. The apparatus of claim 1 wherein the biomolecular separation is performed on a biomolecular material and the biomolecular material comprises DNA, and wherein a first dimension separation is a size-based separation and a second dimension separation is a sequence-based separation.

18. The apparatus of claim 17 wherein the first dimension separation is substantially retained upon transfer to the second dimension.

19. The apparatus of claim 1 further comprising a detector placed near an end of the array of second-dimension microchannels for monitoring the separated biomolecules.

20. The apparatus of claim 1 further comprising measurement means for monitoring DNA fragments resolved from the second separation dimension.

21. The apparatus of claim 1 further comprising an integrated optical detection system.

22. The apparatus of claim 1 further comprising an integrated laser-induced fluorescence detection system.

23. The apparatus of claim 1 further comprising an integrated laser-induced fluorescence detection system capable of simultaneously monitoring each second-dimension microchannels in the array of second-dimension microchannels.

24. The apparatus of claim 1 wherein the at least one first-dimension microchannel include at least a first end and a second end and the second-dimension microchannels include at least first ends and second ends, and further wherein first ends of the second-dimension microchannels terminate at the at least one first-dimension microchannel at one or more points between the first and second ends of the at least one first-dimension microchannel, and wherein an outlet reservoir is in fluid communication with the second ends of the second-dimension microchannels.

25. The apparatus of claim 1 wherein the second-dimension microchannels have first and second ends and the at least one first dimension microchannel intersects the second dimension microchannels at a position somewhere between the first and second ends of the second-dimension microchannels.

26. The apparatus of claim 25 wherein an inlet reservoir is in fluid communication with the first end of the second dimension microchannels and an outlet reservoir is in fluid communication with the second end of the second dimension microchannels.

27. The apparatus of claim 25 wherein the first ends of the second-dimension microchannels terminate at the at least one first-dimension microchannel and further comprising an array of tertiary microchannels having first and second ends, wherein a second end of the tertiary microchannels terminate at the at least one first-dimension microchannel.

28. The apparatus of claim 27 wherein the points at which the second-dimension microchannels intersect with the at least one first-dimension microchannel are staggered with respect to the points at which the tertiary microchannels intersect with the at least one first-dimension microchannel.

29. The apparatus of claim 27 wherein an outlet reservoir is in fluid communication with a second end of the second dimension microchannels and one or more inlet reservoirs are in fluid communication with a first end of the tertiary microchannels.

30. The apparatus of claim 1 further comprising first and second planar substrates and wherein the first and second planar substrates comprise glass.

31. The apparatus of claim 1 further comprising first and second planar substrates and wherein the first and second planar substrates comprise plastic.

32. The apparatus of claim 1 further comprising first and second planar substrates and wherein the first and second planar substrates comprise polycarbonate plastic.

33. The apparatus of claim 1 further comprising first and second planar substrates and wherein the first and second planar substrates comprise a combination of dissimilar materials.

34. The apparatus of claim 1 wherein the at least one first dimension microchannel and the second dimension microchannels have an inner width of between about 5 $\mu$m and about 200 $\mu$m.

35. The apparatus of claim 1 wherein the at least one first dimension microchannel and the second dimension microchannels have an average inner width of between about 5 $\mu$m and about 80 $\mu$m.

36. The apparatus of claim 1 wherein the at least one first dimension microchannel and the second dimension microchannels have an average inner width of between about 5 $\mu$m and about 20 $\mu$m.

37. The apparatus of claim 1 wherein the at least one first dimension microchannel and the second dimension microchannels possess different average widths.

38. The apparatus of claim 1 wherein the at least one first-dimension microchannel has an average width substantially smaller than the second-dimension microchannels.

39. The apparatus of claim 1 wherein the second-dimension microchannels have an average width substantially smaller than the at least one first-dimension microchannel.

40. The apparatus of claim 1 wherein the at least one first dimension microchannel and the second dimension microchannels have an inner depth of between about 5 $\mu$m and about 200 $\mu$m.

41. The apparatus of claim 1 wherein the at least one first dimension microchannel and the second dimension microchannels have an average inner depth of between about 5 $\mu$m and about 80 $\mu$m.

42. The apparatus of claim 1 wherein the at least one first dimension microchannel and the second dimension microchannels have an average inner depth of between about 5 $\mu$m and about 20 $\mu$m.

43. The apparatus of claim 1 wherein the at least one first-dimension microchannel is between about 1 cm and about 50 cm long.

44. The apparatus of claim 1 wherein the at least one first-dimension microchannel is between about 1 cm and about 4 cm long.

45. The apparatus of claim 1 wherein the second-dimension microchannels are between about 1 cm and about 50 cm long.

46. The apparatus of claim 1 wherein the second-dimension microchannels are between about 1 cm and about 4 cm long.

47. The apparatus of claim 1 further comprising an electric field and wherein the electric field along the at least one first-dimension microchannels is between about 100 V/cm and about 1000 V/cm.

48. The apparatus of claim 1 further comprising an electric field and wherein the electric field along the second-dimension microchannels is between about 100 V/cm and about 1000 V/cm.

49. A method for performing two-dimensional biomolecular separations, the method comprising the steps of:
providing at least one first dimension microchannel;
providing an array of second dimension microchannels;
performing a first biomolecular separation in the at least one first dimension microchannel to produce a separated sample;
transferring the separated sample to the array of second dimension microchannels; and
performing a second separation in the second dimension microchannels, where the second separation is performed by applying a temperature gradient.

50. The method of claim 49 wherein the temperature gradient is applied using one or more heating elements affixed to the external surface of a first or a second planar substrate.

51. The method of claim 49 wherein the temperature gradient is applied using one or more heating elements enclosed between a first and second planar substrate, wherein resistive heating of the one or more heating elements produces the temperature gradient.

52. The method of claim 49 wherein the second-dimension microchannels include at least first ends and second ends, and the temperature gradient varies from about 23 degrees Celsius at the intersection between the at least one first-dimension microchannel and the second-dimension microchannel, to about 90 degrees Celsius at a second end of the second-dimension microchannels.

53. The method of claim 49 wherein the second-dimension microchannels include at least first ends and second ends, and the temperature gradient varies from about 23 degrees Celsius at the intersection between the at least one first-dimension microchannel and the second-dimension microchannels, to about 70 degrees Celsius at a second end of the second-dimension microchannels.

54. The method of claim 49 wherein the second-dimension microchannels, include at least first ends and second ends, and the temperature gradient varies from about 90 degrees Celsius at the intersection between the at least one first-dimension microchannel and the second-dimension microchannel, to about 23 degrees Celsius at a second end of the second-dimension microchannels.

55. The method of claim 49 wherein the second dimension microchannels include at least first ends and second ends, and the temperature gradient varies from about 70 degrees Celsius at the intersection between the at least one first-dimension microchannel and the second-dimension microchannel, to about 23 degrees Celsius at a second end of the second-dimension microchannels.

56. The method of claim 49 wherein the temperature gradient is a temporal temperature gradient, wherein;
a) one or more heating elements induce a substantially constant spatial temperature across a length and width of the second-dimension microchannels; and
b) the constant spatial temperature is varied with time.

57. The method of claim 56 wherein the substantially constant spatial temperature is varied from an initial temperature of about 23 degrees Celsius to a final temperature of about 90 degrees Celsius.

58. The method of claim 56 wherein the substantially constant spatial temperature is varied from an initial temperature of about 23 degrees Celsius to a final temperature of about 70 degrees Celsius.

59. The method of claim 56 wherein the substantially constant spatial temperature is varied from an initial temperature of about 90 degrees Celsius to a final temperature of about 23 degrees Celsius.

60. The method of claim 56 wherein the substantially constant spatial temperature is varied from an initial temperature of about 70 degrees Celsius to a final temperature of about 23 degrees Celsius.

61. The method of claim 49 wherein the biomolecular separations are performed on biomolecules and wherein the biomolecules are DNA molecules.

62. A microfluidic apparatus for performing two-dimensional biomolecular separations, the apparatus comprising:
at least one first dimension microchannel;
an array of second dimension microchannels;
an array of tertiary microchannels;
means for performing a first biomolecular separation in the at least one first dimension microchannel to produce a separated sample;
means for electrokinetically transferring the separated sample simultaneously to the second dimension microchannels; and
means for performing a second separation in the second dimension microchannels, where the second separation is performed by applying a temperature gradient.

63. A method for performing two-dimensional biomolecular separations, the method comprising the steps of:
providing at least one first dimension microchannel;
providing an array of second dimension microchannels;
providing an array of tertiary microchannels;
performing a first biomolecular separation in the at least one first dimension microchannel to produce a separated sample; and
electrokinetically transferring the separated sample simultaneously to the second dimension microchannels; and
performing a second separation in the second dimension microchannels, where the second separation is performed by applying a temperature gradient.

64. A method for performing two-dimensional biomolecular separations, the method comprising the steps of:
providing at least one first dimension microchannel;
providing an array of second dimension microchannels;
providing an array of tertiary microchannels;
providing at least one voltage-control microchannel;
performing a first biomolecular separation in the at least one first dimension microchannel to produce a separated sample; and
applying a voltage gradient in the voltage-control microchannels to individually define the voltage within the second-dimension microchannels near the intersections of the at least one first-dimension microchannel and second-dimension microchannels to be nearly equal to the voltage within the at least one first-dimension microchannel near the intersections of the at least one first-dimension microchannel and second-dimension microchannels; and
electrokinetically transferring the separated sample simultaneously to the second dimension microchannels; and
performing a second separation in the second dimension microchannels, where the second separation is performed by applying a temperature gradient.

65. A microfluidic apparatus for performing two-dimensional biomolecular separations, the apparatus comprising:
  a) at least one first-dimension microchannel for receiving a first-dimension separation medium, wherein the at least one first dimension channel has a first end and a second end and extends in a first direction;
  b) an array of one or more second-dimension microchannels for receiving a second-dimension separation medium, wherein the microchannels of the array of one or more second-dimension microchannels each have a first end and a second end, extend in a second direction orthogonal to the first direction and intersect with the at least one first-dimension microchannel;
  c) an array of one or more tertiary microchannels, for providing electrical and fluidic access to one or more points along the at least one first-dimension microchannel, wherein the microchannels of the array of one or more tertiary microchannels each have a first end and a second end, extend in a third direction orthogonal to the first direction and intersect with the at least one first-dimension microchannel;
  d) a first reservoir in fluid communication with the at least one first dimension microchannel,
  e) at least a first electrode, having a first end and a second end, the first end being in electrical communication with the first reservoir,
  f) at least one voltage source in electrical communication with the second end of the first electrode;
  g) at least a second reservoir in fluid communication with microchannels of the array of second dimension microchannels;
  h) at least a second electrode, having a first end and a second end, the first end being in electrical communication with the second reservoir;
  i) at least one voltage source in electrical communication with the second end of the second electrode;
  j) at least a third reservoir in fluid communication with microchannels of the array of tertiary microchannels;
  k) at least a third electrode, having a first end and a second end, the fist end being in electrical communication with the third reservoir; and
  l) at least one voltage source in electrical communication with the second end of the third electrode.

66. A microfluidic apparatus for performing two-dimensional biomolecular separations, the apparatus comprising:
  a) a first planar substrate containing one or more microchannels;
  b) a second planar substrate bonded to the first planar substrate to provide enclosure of the one or more microchannels;
  c) a first-dimension microchannel containing a first-dimension separation medium, wherein the channel has a first end and a second end;
  d) an array of one or more second-dimension microchannels containing a second-dimension separation medium, wherein the microchannels have a first end and a second end, and wherein the one or more second-dimension microchannels intersect the first-dimension microchannel;
  e) an array of one or more tertiary microchannels, wherein the microchannels have a first and a second end, and wherein the one or more tertiary microchannels intersect the first-dimension microchannel;
  f) one or more injection microchannels, wherein the microchannels have a first end and a second end, and wherein the one or more injection microchannels intersect the first-dimension microchannel near the first end of the first-dimension microchannel;
  g) one or more reservoirs formed in the first or second substrate having disposed therein an electrolyte solution and a first end of one or more separation electrodes, and wherein the reservoirs are located at the end of the one or more microchannels;
  h) one or more high voltage power supplies attached to a second end of a selected number of the one or more separation electrodes; and
  i) one or more grounding electrodes attached to the second end of a selected number of the one or more separation electrodes.

67. The apparatus of claim 66 wherein the one or more reservoirs include:
  a) a sample injection inlet reservoir intersecting the first end of the injection microchannel;
  b) a sample injection outlet reservoir intersecting the second end of the injection microchannel;
  c) a first-dimension separation inlet reservoir intersecting the first end of the at least one first-dimension microchannel;
  d) a first-dimension separation outlet reservoir intersecting the second end of the at least one first-dimension microchannel;
  e) one or more second-dimension separation inlet reservoirs intersecting the first end of the one or more second-dimension microchannels; and
  f) one or more second-dimension separation outlet reservoirs intersecting the second end of the one or more second-dimension microchannels.

68. A method of performing two-dimensional gel electrophoresis of biomolecules, comprising:
  a) applying a high electric field along the length of at least one injection microchannel, thereby injecting a sample stream containing the biomolecules of interest from a first end of the at least one injection microchannel towards a second end of the at least one injection microchannel, wherein;
    1) a high voltage is applied to an electrode disposed within an injection outlet reservoir in fluid communication with the second end of the at least one injection microchannel;
    2) a grounding voltage is applied to an electrode disposed within the injection inlet reservoir in fluid communication with the first end of the at least one injection microchannel;
    3) any other reservoirs are disconnected from any voltage source;
    4) the sample stream crosses through a portion of at least one first-dimension microchannel;
  b) applying a high electric field along the length of the at least one first-dimension microchannel, thereby separating the biomolecules based on their migration time through a gel contained therein and resulting in separation of the biomolecules based on their size, wherein;
    1) a high voltage is applied to an electrode disposed within a first-dimension outlet reservoir in fluid communication with a second end of the at least one first-dimension microchannel;
    2) a grounding voltage is applied to an electrode disposed within a first-dimension inlet reservoir in fluid communication with a first end of the at least one first-dimension microchannel;
3) disconnecting any other reservoirs from any voltage source;
4) the separated sample stream passes by one or more second-dimension microchannels intersecting with the at least one first-dimension microchannel;

c) applying a high electric field along the length of one or more second-dimension microchannels while applying a temperature gradient, thereby denaturing the biomolecules and further separating the biomolecules based on their migration time through a gel contained therein, wherein;
1) a spatial temperature gradient is formed along a length of the one or more second-dimension microchannels;
2) a high voltage is applied to an electrode disposed within a second-dimension outlet reservoir in fluid communication with a second end of the one or more second-dimension microchannels;
3) a grounding voltage is applied to an electrode disposed within a second-dimension inlet reservoir in fluidic communication with a first end of the one or more second-dimension microchannels; and
4) disconnecting any other reservoirs from any voltage source.

69. The method of claim 68 wherein a low voltage is applied to the first-dimension outlet reservoir, with a grounding voltage applied to the one or more first-dimension inlet reservoirs, and the second-dimension inlet reservoir is disconnected from any voltage source, during application of the high electric field along the length of the one or more second-dimension microchannels, thereby generating a small electric field along the length of the at least one first-dimension microchannel and causing biomolecules to be drawn slightly towards the first-dimension outlet reservoir to ensure efficient transfer of the biomolecules from the at least one first-dimension microchannel into the one or more second dimension microchannels.

70. The method of claim 68 wherein one or more intersection control voltages are applied to the second-dimension inlet reservoir and the second-dimension outlet reservoir to control electric field lines at intersections of the at least one first-dimension microchannel and the one or more second-dimension microchannels in such a manner that the distribution of biomolecules undergoing separation during the first-dimension separation step are not substantially affected by the intersections.

71. The method of claim 68, further comprising:
one or more voltage control microchannels having first and second ends; and
one or more intersection control voltages that are applied to one or more voltage-control microchannel inlet reservoirs and one or more voltage-control microchannel outlet reservoirs to control electric field lines at intersections of the at least one first-dimension microchannel and the one or more second-dimension microchannels in such a manner that the distribution of biomolecules undergoing separation during the first-dimension separation step are not substantially affected by the intersections.

72. The method of claim 68 wherein one or more intersection control voltages are applied using a plurality of voltage sources, wherein;
a) a first voltage source is connected to a first end of a first resistive element;
b) a second voltage source is connected to a second end of the first resistive element to generate a potential gradient along the first resistive element;
c) the first resistive element is placed in electrical contact with the second-dimension inlet reservoir such that the intersection control voltage at each point of electrical contact is set by the voltage of the first resistive element at the point of electrical contact;
d) the one or more intersection control voltages are chosen such that the voltage near the intersection of the at least one first-dimension microchannel and the one or more second-dimension microchannels at which the intersection control voltage is applied is slightly different than the voltage within the intersection itself,
e) a third voltage source is connected to a first end of a second resistive element;
f) a fourth voltage source is connected to a second end of the second resistive element to generate a potential gradient along the second resistive element;
g) the second resistive element is placed in electrical contact with the second-dimension inlet reservoir such that the intersection control voltage in each reservoir is set by the voltage of the second resistive element at the point of electrical contact;
h) the one or more intersection control voltages are chosen such that the voltage near the intersection of the at least one first-dimension microchannel and the one or more second-dimension microchannels connected to the reservoir at which the intersection control voltage is applied is slightly different than the voltage within the intersection itself.

73. The method of claim 68 wherein one or more intersection control voltages are applied using a plurality of voltage sources, wherein:
a) one voltage source is connected to the inlet reservoir of a first voltage-control microchannel;
b) a second voltage source is connected to an outlet reservoir of the first voltage-control microchannel to generate a potential gradient along the first voltage-control microchannel;
c) the first voltage-control microchannel intersects the one or more second-dimension microchannels such that the intersection control voltage in each second-dimension microchannel is set by the voltage of the inlet reservoir and outlet reservoir of the first voltage-control microchannel;
d) the one or more intersection control voltages are chosen such that the voltage near the intersection of the at least one first-dimension microchannel and the one or more second-dimension microchannels is slightly different than the voltage within the intersection itself,
e) a third voltage source is connected to the inlet reservoir of a second voltage-control microchannel;
f) a fourth voltage source is connected to the outlet reservoir of a second voltage-control microchannel to generate a potential gradient along the second voltage-control microchannel;
g) the second voltage-control microchannel intersects one or more tertiary microchannels such that the intersection control voltage in each tertiary microchannel is set by the voltage of the inlet reservoir and outlet reservoir of the second voltage-control microchannel;
h) the one or more intersection control voltages are chosen such that the voltage near the intersection of the at least one first-dimension microchannel and the one or more tertiary microchannels is slightly different than the voltage within the intersection itself.

* * * * *